US010669558B2

(12) United States Patent
Ganjam

(10) Patent No.: US 10,669,558 B2
(45) Date of Patent: Jun. 2, 2020

(54) STORAGE THROUGH ITERATIVE DNA EDITING

(71) Applicant: Microsoft Technology Licensing, LLC, Redmond, WA (US)

(72) Inventor: Kris K. Ganjam, Seattle, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 0 days.

(21) Appl. No.: 15/623,925

(22) Filed: Jun. 15, 2017

(65) Prior Publication Data
US 2018/0002725 A1 Jan. 4, 2018

Related U.S. Application Data

(60) Provisional application No. 62/357,828, filed on Jul. 1, 2016, provisional application No. 62/399,190, filed on Sep. 23, 2016.

(51) Int. Cl.
C12N 15/90 (2006.01)
C12Q 1/68 (2018.01)

(52) U.S. Cl.
CPC ......... C12N 15/902 (2013.01); C12N 15/905 (2013.01); C12Q 1/68 (2013.01)

(58) Field of Classification Search
None
See application file for complete search history.

(56) References Cited

U.S. PATENT DOCUMENTS

| 7,056,724 | B2 | 6/2006 | Wong et al. |
| 7,659,590 | B2 | 2/2010 | Boland et al. |
| 9,384,320 | B2 | 7/2016 | Church |
| 9,957,526 | B2 | 5/2018 | Holmes et al. |
| 2002/0061528 | A1 | 5/2002 | Gardner et al. |
| 2005/0053968 | A1 | 3/2005 | Bharadwaj et al. |
| 2012/0003630 | A1 | 1/2012 | Collins et al. |
| 2012/0296857 | A1 | 11/2012 | Burns et al. |
| 2014/0315310 | A1 | 10/2014 | Lu et al. |
| 2015/0133315 | A1 | 5/2015 | Jacobson et al. |
| 2015/0225801 | A1 | 8/2015 | Cai et al. |
| 2015/0261664 | A1 | 9/2015 | Goldman et al. |
| 2015/0269313 | A1 | 9/2015 | Church |
| 2015/0368639 | A1 | 12/2015 | Gill et al. |
| 2016/0168592 | A1 | 6/2016 | Church et al. |
| 2016/0312313 | A1 | 10/2016 | Kotula et al. |
| 2016/0333363 | A1 | 11/2016 | Srivastava |
| 2017/0096680 | A1 | 4/2017 | Lu et al. |
| 2017/0369870 | A1 | 12/2017 | Gill et al. |
| 2018/0002748 | A1 | 1/2018 | Ganjam |
| 2018/0004537 | A1 | 1/2018 | Ganjam |
| 2018/0004890 | A1 | 1/2018 | Ganjam |

FOREIGN PATENT DOCUMENTS

| KR | 20150027756 A | 3/2015 |
| KR | 20160001455 A | 1/2016 |
| WO | WO2013/169867 A1 | 11/2013 |
| WO | WO2015/176990 A1 | 11/2015 |
| WO | 2015199614 A1 | 12/2015 |
| WO | WO2016/025719 A1 | 2/2016 |
| WO | 2016040594 A1 | 3/2016 |
| WO | WO2016/059610 A1 | 4/2016 |
| WO | 2016183438 A1 | 11/2016 |
| WO | 2016205728 A1 | 12/2016 |
| WO | 2018005117 A1 | 1/2018 |
| WO | 2018005289 A2 | 1/2018 |
| WO | 2018005289 A3 | 1/2018 |
| WO | 2018005782 A1 | 1/2018 |
| WO | 2018005824 A1 | 1/2018 |

OTHER PUBLICATIONS

Sorek et al., "CRISPR-Mediated Adaptive Immune Systems in Bacteria and Archaea" 82 Annual Review of Biochemistry 237-266 (2013).*
Sun et al., "Recent advances in targeted genome engineering in mammalian systems" 7 Biotechnology Journal 1074-1087 (2012).*
Quétier, "The CRISPR-Cas9 technology: Closer to the ultimate toolkit for targeted genome editing" 242 Plant Science 65-76 (Sep. 8, 2015).*
Packer, Hans, "gBlocks Gene Fragments-Related DECODED Articles", Retrieved from <<https://web.archive.org/web/20150912022743/http://www.idtdna.com/pages/products/genes/gblocks-gene-fragments/decoded-articles/decoded/2013/12/13/crispr-and-cas9-for-flexible-genome-editing>>, Sep. 18, 2015, 4 Pages.
O'Driscoll, et al., "Synthetic DNA: The Next Generation of Big Data Storage", In Journal of Bioengineered, vol. 4, Issue 3, May 2013, pp. 123-125.
Mali, et al., "RNA-Guided Human Genome Engineering via Cas9", In Journal of Science, vol. 339, Issue 6121, Feb. 15, 2013, 8 Pages.
Mali, et al., "Supplementary Information for RNA-Guided Human Genome Engineering via Cas9", In Journal of Science, vol. 339, Issue 6121, Jan. 3, 2013, 36 Pages.
"International Search Report and Written Opinion Issued in PCT Application No. PCT/US2017/037731", dated Sep. 25, 2017, 12 Pages.

(Continued)

Primary Examiner — Nancy J Leith
(74) Attorney, Agent, or Firm — Newport IP, PLLC; Benjamin A. Keim

(57) ABSTRACT

Information is stored in existing DNA through an iterative process of creating a break in dsDNA and adding new DNA by repairing the break with a homologous repair template. The order and sequence of DNA sequences added to the breaks in the dsDNA can encode binary data. By using a context-dependent encoding scheme, three unique homologous repair templates can encode an unbounded number of bits. When the existing DNA is in a cell, the changes are heritably passed to subsequent generations of the cell. Synthesis of the homologous repair templates may be under the control of a promoter and operator. Intra- or extra-cellular signals may regulate the synthesis of homologous repair templates.

21 Claims, 6 Drawing Sheets

Specification includes a Sequence Listing.

(56) References Cited

OTHER PUBLICATIONS

Vishwakarma et al., "High Density Data Storage in DNA Using an Efficient Message Encoding Scheme", In International Journal of Information Technology Convergence and Services (IJITCS), vol. 2, Issue 2, Apr. 2012, pp. 41-46.
Yazdi, et al., "A Rewritable Random-Access DNA-Based Storage System", In Nature Scientific Reports, vol. 5, Issue 14138, May 2013, 10 Pages.
Bonnet, et al., "Rewritable digital data storage in live cells via engineered control of recombination directionality", In Journal of PNAS, vol. 109, No. 23, Jun. 5, 2012, pp. 8884-8889.
Caliando, et al., "Targeted DNA Degradation Using a CRISPR Device Stably Carried in the Host Genome", Nat. Cummun., 2015, 6:6989, 10 pages.
Fusi, et al, "In Silico Predictive Modeling of CRISPR/Cas9 Guide Efficiency", BioRxiv, 2015, http://dx.doi.org/10.1101/021568, 31 pages.
Glaser, et al., "Statistical Analysis of Molecular Signal Recording", PLos Comput. Biol., 2013, vol. 9 (7), e1003145, 14 pages.
Kumar, et al., "Secret data writing using DNA sequences", In Proceedings of International Conference on Emerging Trends in Networks and Computer Communications, Apr. 22, 2011, pp. 402-405.
Limbachiya, et al., "On optimal family of codes for archival DNA storage", In Proceedings of Seventh International Workshop on Signal Design and its Applications in Communications, Sep. 14, 2015, pp. 123-127.
Marblestone, et al., "Physical Principles for Scalable Neural Recording", Frontiers in Computational Neuroscience, 2013, vol. 7, Article 137, 34 pages.
Marblestone, et al., "Rosetta Brains: A Strategy for Molecularly-Annotated Connectomics", 2014, https://arxiv.org/abs/1404.5103, 18 pages.
Shimanovsky, et al., "Hiding Data in DNA", In Proceedings of the Revised Papers from the 5th International Workshop on Information Hiding, Oct. 7, 2002, 15 pages.
Shipman, et al., "Molecular Recordings by Directed CRISPR Spacer Acquisition", Science, 2016, 16 pages.
Tamsir, et al., "Robust Multicellular Computing Using Genetically Encoded NOR Gates and Chemical "Wires"", Nature, 2010, 4 pages.
Yang, et al., "Permanent Genetic Memory with >1-Byte Capacity", Nat. Methods, 2014, vol. 11 (12), pp. 1261-1266.
"Cas9", Retrieved From: https://en.wikipedia.org/wiki/Cas9, Retrieved Date: Sep. 14, 2016, 6 Pages.
"CRISPR interference", Retrieved From: https://en.wikipedia.org/wiki/CRISPR_interference, Retrieved Date: Sep. 14, 2016, 4 Pages.
"CRISPR/CasTools", Retrieved From: https://en.wikipedia.org/wiki/CRISPR/Cas_Tools, Retrieved Date: Sep. 14, 2016, 3 Pages.
"Editas medicine", Retrieved From: http://www.editasmedicine.com/, Retrieved Date: Sep. 14, 2016, 1 Page.
"Gene drive", Retrieved From: https://en.wikipedia.org/wiki/Gene_drive, Retrieved Date: Sep. 14, 2016, 4 Pages.
"Whole organism lineage tracing by combinatorial and cumulative genome editing", Retrieved from: http://dx.doi.org/10.1101/052712, May 11, 2016, 34 Pages.
McKenna, et al., "Whole-organism lineage tracing by combinatorial and cumulative genome editing", In Journal of Science, vol. 353, Issue 6298, Jul. 29, 2016, 27 Pages.
Bate, Geoffrey, "Bits and genes: A comparison of the natural storage of information in DNA and digital magnetic recording", In Proceedings of the IEEE Transactions on Magnetics, vol. 14, Issue 5, Sep. 1, 1978, pp. 964-965.
Aroya, et al., "Making temperature-sensitive mutants", In Journal of Methods Enzymol, Mar. 1, 2010, 23 Pages.
Byrne, Michael, "Scientists Built a Biological Computer inside a Cell", Retrieved From: https://motherboard.vice.com/en_us/article/jpgdgd/engineers-develop-key-building-block-for-sophisticated-biocomputers, Jul. 22, 2016, 4 Pages.
Chu, et al., "Increasing the Efficiency of Homology-directed Repair for CRISPR-Cas9-induced Precise Gene Editing in Mammalian Cells", In Journal of Nature Biotechnology, vol. 33, Issue 5, Mar. 23, 2015, 9 Pages.
Danino, et al., "A Synchronized Quorum of Genetic Clocks", In Journal of Nature, vol. 463, Issue 7279, Jan. 21, 2010, 5 Pages.
Davis, et al., "Homology-directed repair of DNA nicks via pathways distinct from canonical double-strand break repair", In Proceedings of the National Academy of Sciences, vol. 111, Issue 10, Feb. 20, 2014, 9 Pages.
Defrangesco, Ralph M., "Biological Cells as Storage Devices", In Proceedings of the Ninth International Conference on Information Technology—New Generations, Apr. 16, 2012, 3 Pages.
Dow, et al., "Inducible in vivo genome editing with CRISPR-Cas9", In Journal of the Nature Biotechnology, vol. 33, Issue 4, Apr. 1, 2015, 14 Pages.
Espeso, et al., "pH regulation is a major determinant in expression of a fungal penicillin biosynthetic gene", In the EMBO Journal, vol. 12, Issue 10, Oct. 1, 1993, pp. 3947-3956.
Fan, et al., "Combinatorial labeling of single cells for gene expression cytometry", In Proceedings of the Science, vol. 347, Issue 6222, Feb. 5, 2015, 8 Pages.
Fan, et al., "Expression profiling. Combinatorial labeling of single cells for gene expression cytometry", In Proceedings of the Science, vol. 347, Issue 6222, Feb. 6, 2015, 10 Pages.
Farboud, et al., "Dramatic Enhancement of Genome Editing by CRISPR/Cas9 Through Improved Guide RNA Design", In Journal of Genetics, vol. 199, Issue 4, Apr. 1, 2015, 18 Pages.
Farzadfard, et al., "Genomically Encoded Analog Memory with Precise in Vivo DNA Writing in Living Cell Populations", In Journal of Science, vol. 346, Issue 6211, Nov. 14, 2014, 10 Pages.
Gao, et al., "DNA-guided genome editing using the Natronobacterium gregoryi Argonaute", In Journal of Nature Biotechnology, vol. 34, Issue 7, May 2, 2016, pp. 768-773.
Gearing, Mary, "Cpf1: A New Tool for CRISPR Genome Editing", Retrieved From: https://blog.addgene.org/cpf1-a-new-tool-for-crispr-genome-editing, Oct. 14, 2015, 5 Pages.
He, et al. "Knock-in of large reporter genes in human cells via CRISPR/Cas9-induced homology-dependent and independent DNA repair", In Journal of Nucleic Acids Research, vol. 44, Issue 9, Feb. 4, 2016, 14 Pages.
Heid, et al., "Real time quantitative PCR", In the Book of Genome Research, vol. 6, Issue 10, Oct. 1, 1996, pp. 986-994.
Heler, et al., "Mutations in Cas9 Enhance the Rate of Acquisition of Viral Spacer Sequences during the CRISPR-Cas Immune Response", In Journal of Mol Cell, 65, Issue 1, Jan. 5, 2017, 17 Pages.
Hsiao, et al., "A population based temporal logic gate for timing and recording chemical events", In Journal of Molecular Systems Biology, vol. 12, Issue 5, May 17, 2016, 14 Pages.
Hussain, et al., "Engineered temperature compensation in a synthetic genetic clock", In Proceedings of the National Academy of Sciences, vol. 111, Issue 3, Jan. 21, 2014, pp. 972-977.
Irving, Michael, "New record for storing digital data in DNA", Retrieved From: https://newatlas.com/dna-data-storage-record/44273/, Jul. 11, 2016, 17 Pages.
Ji, et al., "Specific Gene Repression by CRISPRi System Transferred through Bacterial Conjugation", Retrieved From: https://www.ncbi.nlm.nih.gov/pmc/articles/PMC4277763/, Dec. 19, 2014, 3 Pages.
Jusiak, et al., "Engineering Synthetic Gene Circuits in Living Cells with CRISPR Technology", In Publication of Trends in biotechnology, vol. 34, Issue 7, Jan. 22, 2016, pp. 535-547.
Kalhor, et al., "Rapidly evolving homing CRISPR barcodes", In Journal of Nature Methods, vol. 14, Issue 2, Feb. 1, 2017, 19 Pages.
Kawane, et al., "DNA Degradation and Its Defects", In Journal of Cold Spring Harbor Perspectives in Biology, vol. 6, Issue 6, Jan. 9, 2018, 15 Pages.
Keskin, et al., "Transcript-RNA-templated DNA recombination and repair", In Journal of Nature, vol. 515, Issue 7527, Nov. 20, 2014, 34 Pages.

(56) References Cited

OTHER PUBLICATIONS

Khoso, Mikal, "Storing Digital Data in DNA", Retrieved From: https://www.northeastern.edu/levelblog/2016/05/18/storing-data-dna/, May 18, 2016, 3 Pages.
Kim, et al., "Synthetic in vitro transcriptional oscillators", In Journal of Molecular Systems Biology, vol. 7, Article No. 465, Feb. 1, 2011, 15 Pages.
Kowalczykowski, "Homologous Recombination Proteins and their Potential Applications in Gene Targeting Technology", Retrieved From: https://web.archive.org/web/20060914085115/http://microbiology.ucdavis.edu/sklab/PDF_files/Kowalczykowski%20and%20Zarling%20(1995)%20Gene%20Targeting%20chapter.pdf, 1995, 44 Pages.
Kowalczykowski, "In vitro reconstitution of homologous recombinaton reactions", Retrieved From: https://web.archive.org/web/20060917235101/http://microbiology.ucdavis.edu/sklab/PDF_files/Kowalczykowski,%201994,%20Experientia,%2050,%20204-215.pdf, Mar. 15, 1994, 13 Pages.
Krejci, et al., "Homologous recombination and its regulation", In Journal of Nucleic Acids Research, vol. 40, Issue 13, Mar. 30, 2012, 24 Pages.
Kulkarni, et al., "Stimulation of Homology-Directed Repair at I-SceI-Induced DNA Breaks during the Permissive Life Cycle of Human Cytomegalovirus", In Journal of Virology, vol. 85, Issue 12, Jun. 15, 2011, 8 Pages.
Kupferschmidt, "Genome editor CRISPR helps trace growth of embryos and maybe cancer next", Retrieved From: http://www.sciencemag.org/news/2016/05/genome-editor-crispr-helps-trace-growth-embryos-and-maybe-cancer-next, May 26, 2016, 13 Pages.
Lafountaine, et al., "Delivery and therapeutic applications of gene editing technologies ZFNs, TALENs, and CRISPR/Cas9", In International Journal of the Pharmaceutics, vol. 494, Issue 1, Aug. 13, 2015, pp. 180-194.
Lakin, et al., "Modelling, Simulating and Verifying Turing-Power, Strand Displacement Systems", In Proceedings of the 17th International Conference on DNA computing and molecular programming, Sep. 19, 2011, pp. 130-144.
Lebar, et al., "A bistable genetic switch based on designable DNA-binding domains", In Proceedings of Nature Communication, vol. 5, Sep. 29, 2014, 13 Pages.
Lee, "Genome editing in vivo with the delivery of Cas9 ribonucleoprotein and donor DNA complexed to gold nanoparticles", In Proceedings of the 5th International Conference and Exhibition on Cell and Gene Therapy, May 19, 2016, 4 Pages.
Lee, et al., "RNA-Guided Genome Editing in *Drosophila* with the Purified Cas9 Protein", Retrieved From: https://www.ncbi.nlm.nih.gov/pubmed/24875628, May 28, 2014, 5 Pages.
Lenz, et al., "Temporal and spatial oscillations in bacteria", In Journal of Nature Reviews Microbiology, vol. 9, Issue 8, Aug. 15, 2011, 13 Pages.
Lewin, "Chapter 8 Recombination of DNA", Retrieved From: http://www.bx.psu.edu/~ross/workmg/RecombineDNACh8.pdf, Retrieved Date: Jun. 27, 2017, 30 Pages.
Li, et al., "Harnessing homologous recombination in vitro to generate recombinant DNA via SLIC", In Journal of Nat Methods, vol. 4, Issue 3, Mar. 1, 2007, 7 Pages.
Macosko, et al., "Highly Parallel genome-wide expression profiling of individual cells using nanoliter droplets", In Proceedings of the Cell, vol. 161, Issue 5, May 1, 2015, pp. 1202-1214.
Maruyama, et al., "Increasing the efficiency of precise genom,e editing with CRISPR-Cas9 by inhibition of nonhomologous end joining", In Journal of Nature biotechnology, vol. 33, Issue 5 , May 1, 2015, 17 Pages.
Addgene, "CRISPR/Cas9 Guide", Retrieved From: https://www.addgene.org/crispr/guide/, Retrieved Date: Sep. 14, 2016, 17 Pages.
Morrical, Scott W., "DNA-Pairing and Annealing Processes in Homologous Recombination and Homology-Directed Repair", In Journal of Cold Spring Harbour Perspectives Biology, vol. 7, Issue 2, Feb. 2, 2015, 20 Pages.

Nelles, et al., "Programmable RNA Tracking in Live Cells with CRISPR/Cas9", In Journal of Cell, vol. 165, Issue 2, Apr. 7, 2016, 19 Pages.
Neupert, et al., "Design of simple synthetic RNA thermometers for temperature-controlled gene expression in *Escherichia coli*", In Journal of Nucleic Acids Research, vol. 36, Issue 19, Aug. 27, 2008, 9 Pages.
Nielsen, et al., "Multi-Input CRISPR/Cas Genetic Circuits That Interface Host Regulatory Networks", In Journal of Molecular Systems Biology, vol. 10, Nov. 24, 2014, 11 Pages.
Nitsche, et al., "Different real-time PCR formats compared for the quantitative detection of human cytomegalovirus DNA", In the Clinical Chemistry, vol. 45, Issue 11, Jan. 1, 1999, pp. 1932-1937.
O'Neill, et al., "Circadian rhythnms persist without transcription in a eukaryote", In Journal of Nature, vol. 467, Issue 7331, Jan. 27, 2011, 11 Pages.
"International Search Report and Written Opinion Issued in PCT Application No. PCT/US2017/039063", dated Jan. 10, 2018, 21 Pages.
"Invitation to Pay Additional Fee Issued in PCT Application No. PCT/US2017/039063", dated Oct. 5, 2017, 12 Pages.
"International Search Report and Written Opinion Issued in PCT Application No. PCT/US2017/039976", dated Oct. 18, 2017, 12 Pages.
"International Search Report and Written Opinion Issued in PCT Application No. PCT/US2017/040046", dated Oct. 10, 2017, 14 Pages.
Perli, et al., "Continuous Genetic Recording with Self-Targeting CRISPR-Cas in Human Cells", In Proceedings of the Science, vol. 353, Issue 6304, Aug. 18, 2016, 4 Pages.
Petersen, "A strand graph semantics for DNA-based computation", In Journal of Theoretical Computer Science, vol. 632, Issue C, Jun. 13, 2016, 50 Pages.
Pierce, et al., "XRCC3 promotes homology-directed repair of DNA damage in mammalian cells", In Proceedings of the Genes & development, vol. 13, Issue 20, 1999, 6 Pages.
Prindle, et al., "A sensing array of radically coupled genetic 'biopixels'", In Journal of Nature, vol. 481, Issue 7379, Dec. 18, 2011, 6 Pages.
Prindle, et al., "Rapid and tunable post-translational coupling of genetic circuits", In Journal of Nature, vol. 508, Issue 7496, Apr. 9, 2014, 16 Pages.
Proudfoot, Nick J. "Ending the message: poly(A) signals then and now", In Journal of Genes & Development, vol. 25, Issue 17, 2011,14 Pages.
Purcell, et al., "A comparative analysis of synthetic genetic oscillators", In Journal of The Royal Society Interface, vol. 7, Issue 52, Nov. 6, 2010, 22 Pages.
Qi, et al., "Repurposing CRISPR as an RNA-guided platform for sequence-specific control of gene expression", In Journal of Cell, vol. 152, Issue 5, Feb. 28, 2013, 11 Pages.
Ran, et al., "Double Nicking by RNA-Guided CRISPR Cas9 for Enhanced Genome Editing Specificity", In Journal of Cell, vol. 154, Issue 6, Sep. 12, 2013, 19 Pages.
Raymond, et al., "Deinococcus radiodurans RNA ligase exemplifies a novel ligase clade with a distinctive N-terminal module that is important for 5'-PO4 nick sealing and ligase adenylylation but dispensable for phosphodiester formation at an adenylylated nick", In Journal of Nucleic Acids Research, vol. 35, Issue 3, Jan. 4, 2007, 11 Pages.
Reilly, Patrick, "Why is mRNA fed into the CRISPR Cas9 system and not DNA?", Retrieved From: https://www.quora.com/Why-is-mRNA-fed-into-the-CRISPR-Cas9-system-and-not-DNA, Jun. 5, 2015, 3 Pages.
Roquet, et al., "Synthetic recombinase-based state machines in living cells", Retrieved From: http://science.sciencemag.org/content/353/6297/aad8559.long, Jul. 22, 2016, 1 Page.
Ryback, et al., "Design and Analysis of a Tunable Synchronized Oscillator", In Journal of the Biological Engineering, vol. 7, Issue 1, Nov. 18, 2013,10 Pages.
Sekiguchi, et al., "Ligation of RNA-Containing Duplexes by Vaccinia DNA Ligase", In Journal of Biochemistry, vol. 36, Issue 29, Jul. 22, 1997, 1 Page.

(56) References Cited

OTHER PUBLICATIONS

Silas, et al., "Direct CRISPR spacer acquisition from RNA by a natural reverse transcriptase-Cas1 fusion protein", In Journal of Science, vol. 351, Issue 6276, Feb. 26, 2016, 31 Pages.
Sriskanda, et al., "Specificity and fidelity of strand joining by Chlorella virus DNA ligase", In Journal of Nucleic Acids Research, vol. 26, Issue 15, Aug. 1, 1998, 6 Pages.
Stricker, et al., "A fast, robust and tunable synthetic gene oscillator", In Proceedings of Nature, vol. 456, Issue 7221, Nov. 27, 2008, 38 Pages.
Tigges, et al., "A tunable synthetic mammalian oscillator", In Journal of Nature, vol. 457, Jan. 15, 2009, Issue 7227, 4 Pages.
Trafton, Anne, "Engineers program human cells to store complex histories in their DNA", Retrieved From: https://phys.org/news/2016-08-human-cells-complex-histories-dna.html, Aug. 18, 2016, 4 Pages.
Trafton, Anne, "Human DNA cells genetically engineered to store memories and complex histories", Retrieved From: https://futuristech.info/posts/human-dna-cells-genetically-engineered-to-store-memories-and-complex-histories/, Aug. 23, 2016, 3 Pages.
Tsai, et al., "Robust, Tunable Biological Oscillatons from Interlinked Positive and Negative Feedback Loops", In Journal of Science, vol. 321, Issue 5885, Jul. 4, 2008, 19 Pages.
Unciuleac, et al., "Characterization of a novel eukaryal nick-sealing RNA ligase from Naegleria Gruberi", In Journal of RNA, vol. 21, Issue 5, May 1, 2015, 9 Pages.
Waters, Virginia L., "Conjugation between bacterial and mammalian cells", In Journal of Nature Genetics, vol. 29, Issue 4, Nov. 19, 2001, 4 Pages.
Weinberg, et al., "Large-scale design of robust genetic circuits with multiple inputs and outputs for mammalian cells", In Journal of Nature Biotechnology, vol. 35, Issue 5, May 1, 2017, 13 Pages.
Weintraub, Karen, "CRISPR gene-editing system unleashed on RNA", Retrieved From: https://www.nature.com/news/crispr-gene-editing-system-unleashed-on-rna-1.20030, Jun. 3, 2016, 4 Pages.
Williams, Sarah, "DNA tape recorder stores a cell's memories", Retrieved From: http://www.sciencemag.org/news/2014/11/dna-tape-recorder-stores-cells-memories, Nov. 13, 2014, 7 Pages.
Woods, Mae, et al., "A Statistical Approach Reveals Designs for the Most Robust Stochastic Gene Oscillators", In Publication of ACS Synthetic Biology, vol. 5, Issue 6, Jun. 17, 2016, 39 Pages.
Wu, et al., "Target specificity of the CRISPR-Cas9 system", In Journal of Quantitative Biology, vol. 2, Issue 2, Jun. 1, 2014, 19 Pages.
Yang, et al., "Enrichment of G2/M cell cycle phase in human pluripotent stem cells enhances HDR-mediated gene repair with customizable endonucleases", Retrieved From: https://www.ncbi.nlm.nih.gov/pmc/articles/PMC4757933/pdf/srep21264.pdf, Feb. 18, 2016, 15 Pages.
Yin, et al., "Thereapeutic genome editing by combined viral and non-viral delivery of CRISPR system components in vivo", In Journal of Nature Biotechnology, vol. 34, Issue 3, Mar. 1, 2016, 15 Pages.
Yordanov, et al., "Functional Analysis of Large-scale DNA Strand Displacement Circuits", In Journal of International Conference on DNA Computing and Molecular Programming, vol. 8141, Sep. 1, 2013, pp. 189-203.
Yosef, et al., "Proteins and DNA elements essential for the CRISPR adaptation process in *Escherichia coli*", In Journal of Nucleic Acids Research, vol. 40, Issue 12, Mar. 8, 2012, 8 Pages.
Zuris, et al., "Cationic lipid-mediated delivery of proteins enables efficient protein-based genome editing in vitro and in vivo", In Journal of Nature Biotechnology, vol. 33, Issue 1, Oct. 30, 2014, 49 Pages.
McDade, Joel, "The PAM Requirement and Expanding CRISPR Beyond SpCas9", Retrieved From: https://blog.addgene.org/the-pam-requirement-and-expanding-crispr-beyond-spcas9, Nov. 12, 2015, 6 Pages.
"Restriction Requirement Issued in U.S. Appl. No. 15/626,020", dated Jul. 12, 2018, 8 Pages.
"Non-Final Office Action Issued in U.S. Appl. No. 15/626,021", dated Sep. 24, 2018, 10 Pages.
"Restriction Requirement Issued in U.S. Appl. No. 15/626,021", dated Jun. 26, 2018, 6 Pages.
Findlay, et al., "Saturation editing of genomic regions by multiplex homology". In Nature, vol. 513, Sep. 4, 2014, 16 Pages.
"Non Final Office Action Issued in U.S. Appl. No. 15/626,020", dated Oct. 31, 2018, 17 Pages.
Paquet, et al., "Efficient Introduction of Specific Homozygous and Heterozygous Mutations Using CRISPR/Cas9", In Journal Nature, vol. 533, Issue 7601, Apr. 27, 2016, pp. 125-129.
Wang, et al., "Genetic screens in human cells using the CRISPR/Cas9 system", Retrieved from: https://www.ncbi.nlm.nih.gov/pmc/articles/PMC3972032/, Jan. 3, 2014, pp. 80-84.
"Final Office Action Issued in U.S. Appl. No. 15/626,021", dated Feb. 11, 2019, 7 Pages.
"Non Final Office Action Issued in U.S. Appl. No. 15/625,998", dated Jul. 18, 2019, 27 Pages.
Andrianantoandro, et al., "Synthetic Biology: New Engineering Rules for an Emerging Discipline", In Journal of Molecular Systems Biology, EMBO and Nature Publishing Group, May 2006, pp. 1-14.
Schmidt, et al., "Applications of CRISPR-Cas for Synthetic Biology and Genetic Recording", In Journal of Current Opinion in System Biology, vol. 5, Oct. 2017, pp. 9-15.
Sheth, et al., "DNA-based Memory Devices for Recording Cellular Events", In Journal of Nature Reviews Genetics, Sep. 20, 2018, 30 Pages.
Wikipedia, "Homology Directed Repair", Retrieved From: https://en.wikipedia.org/wiki/Homology_directed_repair, Jul. 15, 2019, 4 Pages.
"Non Final Office Action Issued in U.S. Appl. No. 15/626,021", dated Jul. 12, 2019, 10 Pages.
"Final Office Action Issued in U.S. Appl. No. 15/626,020", dated May 31, 2019, 17 Pages.
Wingler, et al., "Reiterative Recombination for the in vivo assembly of libraries of multigene pathways", In Proceedings of the National Academy of Sciences, Sep. 13, 2011, 6 Pages.
"Search Report Issued in European patent Application No. 19185657.4", dated Dec. 9, 2019, 8 Pages.
"Final Office Action Issued in U.S. Appl. No. 15/626,021", dated Nov. 22, 2019, 9 Pages.
"Final Office Action Issued in U.S. Appl. No. 15/625,998", dated Dec. 6, 2019, 15 Pages.
"Office Action Issued in European Patent Application No. 17742885.1", dated Feb. 20, 2020, 7 Pages.

\* cited by examiner

STORAGE THROUGH ITERATIVE DNA EDITING

RELATED APPLICATIONS

This application claims priority to U.S. Patent Application Ser. No. 62/357,828, filed on Jul. 1, 2016, and entitled "Storage Through Iterative DNA Editing," and to U.S. Patent Application Ser. No. 62/399,190, filed on Sep. 23, 2016, and entitled "Storage Through Iterative DNA Editing," which are both incorporated herein by reference.

BACKGROUND

The ability to store and retrieve arbitrary information within existing deoxyribose nucleic acids (DNA) such as the DNA in cells is an important goal for synthetic biology that has the potential to create a low-cost, high-density storage medium for binary data. To date, existing storage methods within cells have been able to record only up to a few bytes of information, but require specialized, orthogonal genetic constructs for each bit, greatly limiting the maximum storage capacity.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Precise gene editing techniques such as CRISPR/Cas (Clustered regularly interspaced short palindromic repeats/CRISPR associated protein) system and TALEN (transcription activator-like effector nucleases) enables manipulation of DNA in ways that can be used to store arbitrary information, or state information of a cell. The methods described herein is capable of dynamically recording an unbounded amount of binary data within a live cell by incremental editing of cellular DNA using gene editing techniques. The information may be transduced from any intra- or extra-cellular signal and is permanently recorded in the DNA in a manner that allows the information to be passed to subsequent cellular generations. This method may also be used in cell-free or synthetic cell systems.

DNA in a cell, or in another environment such as a cell free system, may be cut to create a double strand break ("DSB"). New DNA may be inserted into the break using homology directed repair (HDR). Thoughtful design of a target site in the original DNA as well as design of homologous repair templates makes it possible to repeatedly cut the DNA and add new DNA within the cut thereby adding DNA within an existing strand of DNA in a way that encodes binary data or other information.

The sequence of additions may encode 0s and 1s allowing for storage of arbitrary binary data in a way that is heritably passed to new cells during cell division. Signaling pathways may be used to control the insertion of specific homologous repair templates and/or availability of specific enzymes in order to direct the cell to record either a 0 or a 1.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
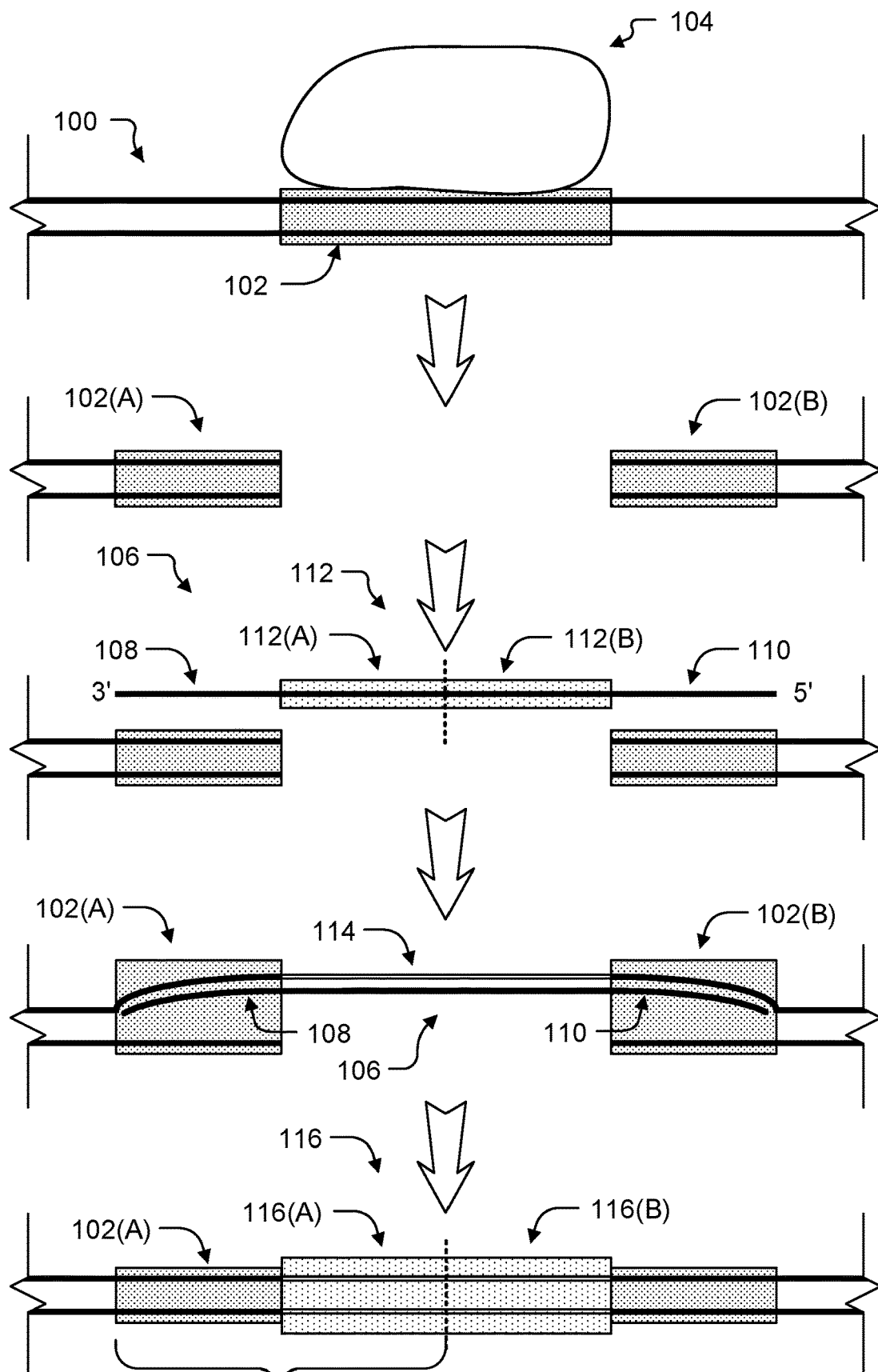
FIG. 1 shows a schematic representation of cutting dsDNA with an enzyme and inserting new DNA by homology directed repair.

There are many techniques for encoding binary data in the sequence of a nucleic acid. Most of those techniques are based on synthesizing new nucleic acids and strive for a compact encoding in which only a few nucleic acid bases are needed to encode a 1 or 0. However, the technique described in this disclosure adds new DNA sequences in the middle of an existing DNA to encode binary data. Due to the constraints of working on existing DNA that involves manipulation with enzymes, the presence of binding sites, etc. the encoding is not as compact as it could be in a system that uses newly synthesized DNA.

The technique of this disclosure stores data in DNA by repeatedly cutting and inserting a new sequence into the existing DNA. Each insert provides within the insert a target site for the next round of DNA cutting and subsequent insertion. Repeating this process creates a DNA molecule with a series of nested inserts. The order of the nested inserts may be interpreted as encoding a series of 1s and 0s.

By "hybridizable" or "complementary" or "substantially complementary" it is meant that a nucleic acid (e.g. DNA) comprises a sequence of nucleotides that enables it to non-covalently bind, to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). In the context of this disclosure, a guanine (G) is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature ($T_m$) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature, pH, and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

FIG. 1 shows an illustrative schematic of operations to add a new DNA sequence into a double-stranded DNA (dsDNA) 100. The dsDNA 100 includes a target site 102 that directs an enzyme 104 to create a DSB in the dsDNA 100 within the target site 102. The DSB may be created with blunt ends or with sticky ends depending on the specific enzyme and technique for making the DSB. The target site 102 is a sequence of DNA recognized by an enzyme that creates DSBs in dsDNA. The target site 102 may be intentionally introduced into the dsDNA 100 to enable the manipulations described below. Alternatively, a pre-existing portion of the dsDNA 100 may be selected as the target site 102. If a pre-existing portion of the dsDNA 100 is selected as the target site 102, then the sequence of other components of the system will be designed with reference to the sequence of the target site 102. In some implementations, the target site 102 is unique such that there is only one target site 102 in the entire dsDNA strand. The dsDNA 100 may be genomic DNA inside a living prokaryotic or eukaryotic cell, DNA introduced to a living cell such as a plasmid or vector, or DNA in a cell free system. The dsDNA 100 may exist as either linear or circular DNA prior to introduction of the DSB.

The enzyme 104 that creates the DSB may be any protein, protein-RNA complex, or protein-DNA complex (including multimeric complexes) that has the property of creating a DSB in dsDNA at a specific target site. Non-limiting examples of suitable enzymes include restriction enzymes, homing endonucleases, zinc-finger nucleases (ZFNs), transcription activator-like effector nucleases (TALENs), and CRISPR/Cas. These types of enzymes listed above are all examples of site-specific nucleases that are capable of causing a DSB within a target site.

Restriction enzymes (restriction endonucleases) are present in many species and are capable of sequence-specific binding to DNA (at a target or recognition site), and cleaving DNA at or near the site of binding. Over 3000 restriction enzymes have been studied in detail, and more than 600 of these are available commercially. Naturally occurring restriction endonucleases are categorized into four groups (Types I, II III, and IV) based on their composition and enzyme cofactor requirements, the nature of their target sequence, and the position of their DNA cleavage site relative to the target sequence. All types of enzymes recognize specific short DNA sequences and carry out the endonucleolytic cleavage of DNA to give specific fragments with terminal 5'-phosphates. One type of restriction enzyme, Type II enzymes, cleave within or at short specific distances from a recognition site; most require magnesium; single function (restriction) enzymes independent of methylase. Type II enzymes form homodimers, with recognition sites that are usually undivided and palindromic and 4-8 nucleotides in length. They recognize and cleave DNA at the same site, and they do not use ATP or AdoMet for their activity—they usually require only $Mg^{2+}$ as a cofactor. Common type II restriction enzymes include HhaI, HindIII, NotI, EcoRI, and BglI. Restriction enzymes may cut dsDNA in a way that leaves either blunt ends or sticky ends. Protocols for creating a DSB in dsDNA with restriction enzymes are well known to those skilled in the art. Restriction digest is a common molecular biology technique and is typically performed using the reagents and protocols provided in a commercially available restriction digest kit. Examples of companies that provide restriction digest kits include New England BioLabs, Promega, Sigma-Aldrich, and Thermo Fisher Scientific. Each of these companies provides restriction digest protocols on their website.

Homing endonucleases (HEs), which are also known as meganucleases, are a collection of double stranded DNases that have large, asymmetric recognition sites (12-40 base pairs) and coding sequences that are usually embedded in either introns or inteins. Introns are spliced out of precursor RNAs, while inteins are spliced out of precursor proteins. They catalyze the hydrolysis of genomic DNA within the cells that synthesize them, but do so at very few, or even singular, locations. HE recognition sites are extremely rare. For example, an 18 base pair recognition sequence will occur only once in every $7 \times 10^{10}$ base pairs of random sequence. This is equivalent to only one site in 20 mammalian-sized genomes. However, unlike restriction endonucleases, HEs tolerate some sequence degeneracy within their recognition sequence. Thus, single base changes do not abolish cleavage but reduce its efficiency to variable extents. As a result, their observed sequence specificity is typically in the range of 10-12 base pairs. Examples of suitable protocols using HEs may be found in Karen Flick et al., *DNA Binding in Cleavage by the Nuclear Introns-Encoded Homing Endonuclease I-Ppol*, 394 Nature 96-101 (1998) and Brett Chevalier et al., *Design, Activity, and Structure of a Highly Specific Artificial Endonuclease*, 10 Molecular Cell 895-905 (2002).

Zinc finger nucleases (ZFNs) are synthetic proteins consisting of an engineered zinc finger DNA-binding domain fused to the cleavage domain of the FokI restriction endonuclease. ZFNs can be used to induce DSBs in specific DNA sequences and thereby promote site-specific homologous recombination and targeted manipulation of genomic loci in a variety of different cell types. The introduction of a DSB into dsDNA may enhance the efficiency of recombination with an exogenously introduced homologous repair template. ZFNs consist of a DNA-binding zinc finger domain (composed of three to six fingers) covalently linked to the non-specific DNA cleavage domain of the bacterial FokI restriction endonuclease. ZFNs can bind as dimers to their target DNA sites, with each monomer using its zinc finger domain to recognize a half-site. Dimerization of ZFNs is mediated by the FokI cleavage domain which cleaves within a five or six base pair "spacer" sequence that separates the two inverted "half sites." Because the DNA-binding specificities of zinc finger domains can in principle be re-engineered using one of various methods, customized ZFNs can be constructed to target nearly any DNA sequence. One of ordinary skill in the art will know how to design and use ZFNs to create DSBs in dsDNA at a desired target site. Some suitable protocols are available in Philipsborn, A, et al., Nature Protocols, 2006, 1, 1322-1328; John Young and Richard Harland, *Targeted Gene Disruption with Engineered Zinc Finger Nucleases (ZFNs)*, 917 Xenopus Protocols 129-141 (2012), and Hansen, K., et al. *Genome Editing with CompoZr Custom Zinc Finger Nucleases (ZFNs)*. J. Vis. Exp. 2012, 64, e3304, doi:10.3791/3304.

TALEN are restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ. The DNA binding domain contains a repeated highly conserved 33-34 amino acid sequence with divergent $12^{th}$ and $13^{th}$ amino acids. These two positions, referred to as the Repeat Variable Diresidue (RVD), are highly variable and show a strong correlation with specific nucleotide recognition. This straightforward relationship between amino acid sequence and DNA recognition has allowed for the engineering of specific DNA-binding domains by selecting a combination of repeat segments containing the appropriate RVDs. Notably, slight changes in the RVD and the incorporation of "nonconventional" RVD sequences can improve targeting specificity. One of ordinary skill in the art will know how to design and use TALENs to create DSBs in dsDNA at a desired target site. Some suitable protocols are available in Marlo Hermann et al., *Mouse Genome Engineering Using Designer Nucleases*, 86 J. Vis. Exp. e50930, doi:10.3791/50930 (2014) and Tetsuhi Sakuma et al., *Efficient TALEN Construction and Evaluation Methods for Human Cell and Animal Applications*, 18(4) Genes Cells 315-326 (2013).

In the CRISPR/Cas nuclease system, the CRISPR locus, encodes RNA components of the system, and the Cas (CRISPR-associated) locus, encodes proteins. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA DSB in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. The Cas9 species of different organisms have different PAM sequences. For example, *Streptococcus pyogenes* (Sp) has a PAM sequence of 5'-NGG-3', *Staphylococcus aureus* (Sa) has a PAM sequence of 5'-NGRRT-3' or 5'-NGRRN-3', *Neisseria meningitidis* (NM) has a PAM sequence of 5'-NNNNGATT-3', *Streptococcus thermophilus* (St) has a PAM sequence of 5'-NNAGAAW-3', *Treponema denticola* (Td) has a PAM sequence of 5'-NAAAAC-3'.

Finally, Cas9 mediates cleavage of target DNA to create a double-stranded break within the protospacer. Activity of the CRISPR/Cas system comprises three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA, etc.

CRISPR may also function with nucleases other than Cas9. Two genes from the Cpfl family contain a RuvC-like endonuclease domain, but they lack Cas9's second HNH endonuclease domain. Cpfl cleaves DNA in a staggered pattern and requires only one RNA rather than the two (tracrRNA and crRNA) needed by Cas9 for cleavage. Cpfl's preferred PAM is 5'-TTN, differing from that of Cas9 (3'-NGG) in both genomic location and GC-content. Mature crRNAs for Cpfl-mediated cleavage are 42-44 nucleotides in length, about the same size as Cas9's, but with the direct repeat preceding the spacer rather than following it. The Cpfl crRNA is also much simpler in structure than Cas9's; only a short stem-loop structure in the direct repeat region is necessary for cleavage of a target. Cpfl also does not require an additional tracrRNA. Whereas Cas9 generates blunt ends 3 nt upstream of the PAM site, Cpfl cleaves in a staggered fashion, creating a 5 nucleotide 5' overhang 18-23 bases away from the PAM.

There are also CRISPR/Cas9 variants that do not use a PAM sequence such as NgAgo. NgAgo functions with a 24 nucleotide ssDNA guide and is believed to cut 8-11 nucleotides from the start of this sequence. The ssDNA is loaded as the protein folds and cannot be swapped to a different guide unless the temperature is increased to non-physiological 55° C. A few nucleotides in the target DNA are removed near the cut site. Techniques for using NgAgo are described in Feng Gao et al., *DNA-guided Genome Editing Using the Natronobacterium Gregoryi Argonaute*, 34 Nature Biotechnology 768-770 (2016).

DSBs may be formed by making two single-stranded breaks at different locations creating a cut DNA molecule with sticky ends. Single-strand breaks or "nicks" may be formed by modified versions of the Cas9 enzyme containing only one active catalytic domain (called "Cas9 nickase"). Cas9 nickases still bind DNA based on gRNA specificity, but nickases are only capable of cutting one of the DNA strands. Two nickases targeting opposite strands are required to generate a DSB within the target DNA (often referred to as a "double nick" or "dual nickase" CRISPR system). This requirement dramatically increases target specificity, since it is unlikely that two off-target nicks will be generated within close enough proximity to cause a DSB.

In certain embodiments, any of the enzymes mentioned above may be a "functional derivative" of a naturally occurring protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of an enzyme or a fragment thereof include but are not limited to mutants, fusions, covalent modifications of the protein or a fragment thereof. The enzyme, or a fragment thereof, as well as derivatives or a fragment thereof, may be obtainable from a cell or synthesized chemically or by a combination of these two procedures. The cell may be a cell that naturally produces the enzyme. A cell that naturally produces enzyme may also be genetically engineered to produce the endogenous enzyme at a higher expression level or to produce the enzyme from an exogenously introduced nucleic acid, which nucleic acid encodes an enzyme that is the same or different from the endogenous enzyme. In some cases, a cell does not naturally produce the enzyme and is genetically engineered to produce the enzyme.

After creating a DSB in the target site 102, the target site 102 is split into two subsequences 102(A), 102(B) on either side of the DSB. Each of the two subsequences 102(A), 102(B) may be between 5 and 20 nucleotides in length. Thus, the target site 102 may be between 10 and 40 nucleotides in length. In some implementations, the two subsequences 102(A), 102(B) may contain identical DNA sequences. The DSB may be located in the middle of the target site 102 or it may be located elsewhere within the target site 102. The schematic shown in FIG. 1 illustrates a DSB with blunt ends, but as described above DSBs with sticky ends are also covered within the scope of this disclosure.

A homologous repair template 106 is brought into proximity of the dsDNA 100 with the DSB. The homologous repair template 106 is single strand (ss) DNA or ssRNA. The homologous repair template 106 includes a 3'-end sequence 108 complementary to the first subsequence of the target site 102(A) and a 5'-end sequence 110 complementary to a second subsequence of the target site 102(B). Because they are complementary sequences, the length of the 3'-end sequence 108 and the 5'-end sequence 110 are the same or about the same as the respective subsequences of the target site 102(A), 102(B). Thus, both 3'-end sequence 108 and the 5'-end sequence 110 may be between 5 and 20 nucleotides in length. The middle portion of the homologous repair template 106 contains a region 112 encoding a second target site 116. This middle region 112 may contain two subsequences 112(A), 112(B) on either side of the point where the second target site 116 will be cut by a second enzyme. The length of the two subsequences 112(A), 112(B) in the middle portion 112 of the homologous repair template 106 may be different than the lengths of the two subsequences 102(A), 102(B) but may follow the same size range and be between five and 20 nt in length. Thus, the total length of the homologous repair template 106 may be between about 20 and 80 nt. Because the middle region 112 encodes a second target site 116, the homologous repair template 106 itself provides the basis for this process to be repeated iteratively.

The homologous repair template 106 repairs the DSB through homology-directed repair (HDR). HDR is a mechanism in cells to repair double strand DNA lesions. HDR includes homologous recombination (HR) and single-strand annealing (SSA) (Lieber. 2010 Annu. Rev. Biochem. 79:181-211). The most common form of HDR is HR which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932).

An overabundance of the homologous repair template 106 may be provided to increase efficiency of HDR. The overabundance of homologous repair template 106 may be provided to a cell free system by adding additional copies of the ssRNA or ssDNA manually or with the use of microfluidics. The homologous repair template 106 may also be provided, in overabundance if desired, by placing a gene encoding for the homologous repair template 106 under control of a strong promoter and/or by having multiple copies of the gene encoding the homologous repair template 106 under the control of the same promoter.

The 5'-ended DNA strand is resected at the break to create a 3' overhang. This will serve as both a substrate for proteins required for strand invasion and a primer for DNA repair synthesis. The homologous repair template 106 can then displace one strand of the homologous DNA duplex and pair with the other; this causes formation of hybrid DNA referred to as the displacement loop ("D loop"). The recombination intermediates can then be resolved to complete the DNA repair process. As mentioned above, an overabundance of the homologous repair template 106 may be provided. One of ordinary skill in the art will understand how to perform HDR with dsDNA 100 having a DSB and a homologous repair template 106. Possible protocols for performing HDR are provided in Jie Liu et al., *In Vitro Assays for DNA Pairing in Recombination-Associated DNA Synthesis*, 745 Methods Mol. Bio. 363-383 (2011); Gratz, S, et al., 196 Genetics 967-971 (2014); Richardson, C, et al., 34 Nature Biotechnology 399-344 (2016); and Lin, S, et al., *eLIFE*, 2014, 3:e04766.

After the homologous repair template 106 invades the dsDNA the D loop is formed by hybridization of the 3'-end sequence 108 to the first subsequence 102(A) of the target site 102 and hybridization of the 5'-end sequence 110 to the second subsequence 102(B) of the target site 102. DNA polymerase synthesizes new ssDNA 114 complementary to the middle portion 112 of one strand of the dsDNA 100. DNA ligase joins the sugar-phosphate backbone of the newly synthesized ssDNA 114 with the remainder of that strand of the dsDNA 100. This forms one strand of the second target site 116.

Following repair of the first strand of the dsDNA 100, the second strand of the dsDNA 100 is repaired by DNA polymerase and DNA ligase using the sequence of the new ssDNA 114 in the repaired, first strand as a template. This completes the repair of the dsDNA 100 resulting in dsDNA that includes the second target site 116 inserted within the first target site 102.

DNA polymerases are enzymes that synthesize DNA molecules from individual deoxyribonucleotides. During this process, DNA polymerase "reads" an existing DNA strand to create a new, complementary strand. DNA ligase is a specific type of enzyme, a ligase, that facilitates the joining of DNA strands together by catalyzing the formation of a phosphodiester bond. It plays a role in repairing single-strand breaks. The mechanism of DNA ligase is to form two covalent phosphodiester bonds between 3' hydroxyl ends of one nucleotide, ("acceptor") with the 5' phosphate end of another ("donor"). The DNA ligase from bacteriophage T4 is the ligase most-commonly used in laboratory research. It can ligate cohesive or "sticky" ends of DNA, oligonucleotides, as well as RNA and RNA-DNA hybrids, but not single-stranded nucleic acids. It can also ligate blunt-ended DNA.

Note that the homologous repair template 106 includes two types of regions: end regions and a middle region. The end regions are homologous to one of the strands of the dsDNA 100 on either side of the DSB. Here, the homologous regions are shown by the 3'-end sequence 108 and the 5'-end sequence 110. The homology need not be 100% but only to the extent that the 3'-end sequence 108 and the 5'-end sequence 110 hybridize to one strand of the dsDNA 100. The middle region is the middle portion 112 of the homologous repair template 106 that encodes the sequence of the second target site 116. Independently varying both the end regions and the middle region allows for creation of multiple different homologous repair templates 106 from a relatively limited set of end regions and middle regions.

Following HDR the dsDNA 100 includes the first subsequence 102(A) of the first target site 102 followed by the first subsequence 116(A) of the second target site 116. The DNA sequence 118 represented by this order of the two subsequences 102(A), 116(A) of the two target sites represents a binary digit (e.g., 0 or 1). As mentioned above, a length of the subsequence 102(A) is from five to 20 nucleotides and the length of the subsequence 112(A) is also from five to 20 nucleotides. Thus, the bit represented by the DNA sequence 118 is encoded by a sequence of 10 to 40 nucleotides. More precisely, the bit is encoded by a first sequence of five to 20 nucleotides being adjacent to a second sequence of five to 20 nucleotides rather than by the specific identity of each of the five to 20 nucleotides.

Figure 2:
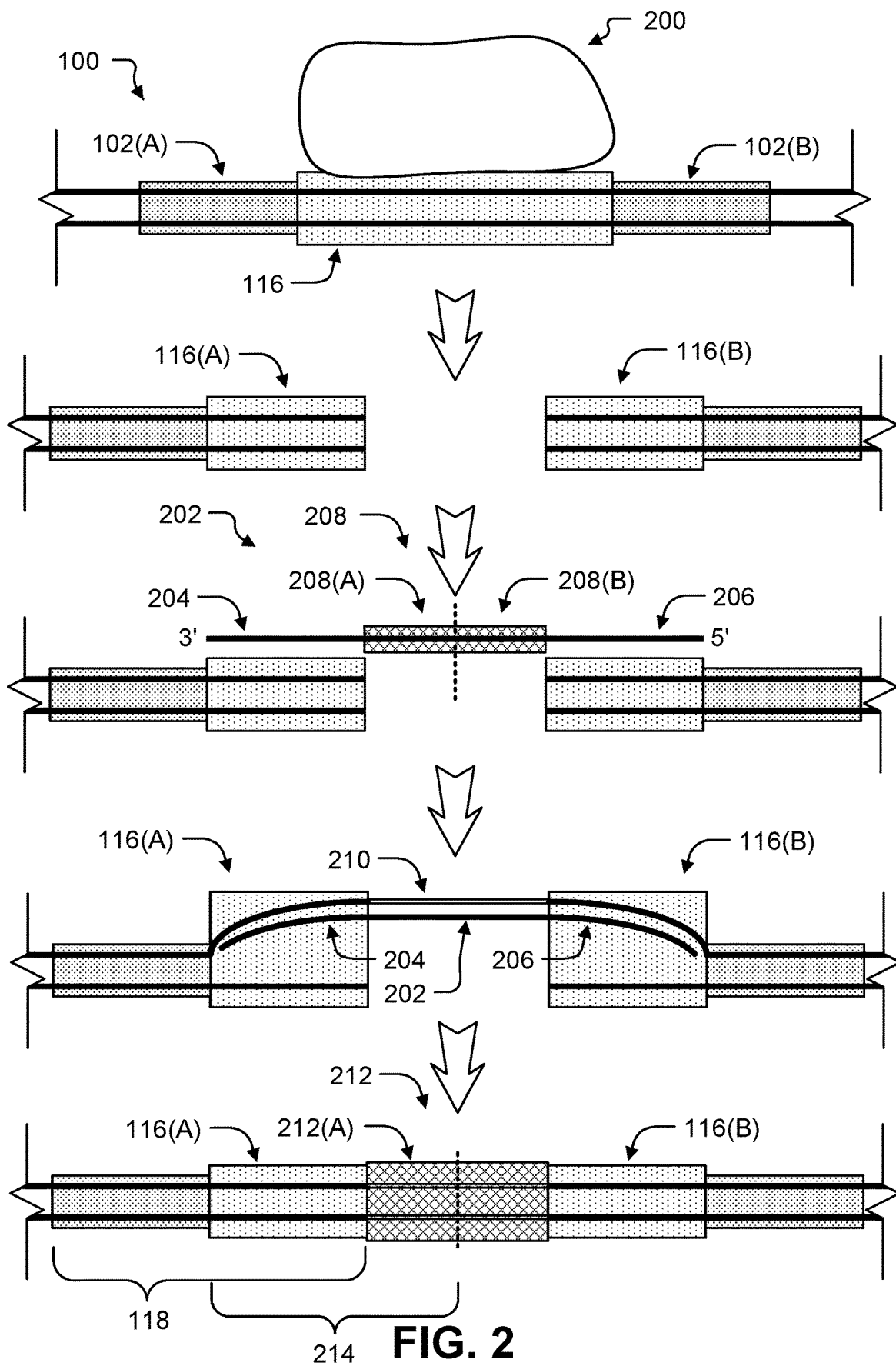
FIG. 2 shows a schematic representation of cutting the dsDNA of FIG. 1 and inserting additional DNA by homology directed repair.

FIG. 2 shows schematic illustrations of further manipulations performed on the dsDNA 100 molecule of FIG. 1. The second enzyme 200 creates a second DSB in the second target site 116. The second target site 116 has a different sequence than the first target site 102, and thus, the second enzyme 200 recognizes a different DNA sequence than the first enzyme 104. Creating a DSB in the second target site 116 creates the first subsequence 116(A) of the second target site 116 on one side of the DSB and a second subsequence 116(B) of the second target site 116 on the other side of the DSB. In some implementations, the first subsequence 116(A) and the second subsequence 116(B) may have the same sequence. Thus, the first subsequence 116(A) and a second subsequence 116(B) may have the same nucleotide length. Also, if the first subsequence 116(A) and the second subsequence 116(B) are the same sequence, the second target site 116 may be thought of as having a single subsequence repeated once.

A second homologous repair template 202 contacts the dsDNA 100 to provide a template for HDR of the DSB. The second homologous repair template 202 includes a 3'-end region 204 that is homologous to one strand of the dsDNA 100 within the first subsequence 116(A) of the second target site 116. The second homologous repair template 202 also include a 5'-end region 206 that is homologous to one strand of the dsDNA 100 within the second subsequence 116(B) of the second target site 116. The second homologous repair template 202 also includes a portion in the middle 208 that encodes a third target site 212 for a third enzyme. The middle region 208 includes a first subsequence 208(A) on one side of the DSB and a second subsequence 208(B) on other side of the DSB.

Annealing of the second homologous repair template 202 to one strand of the dsDNA 100 creates a D loop by hybridization of the 3'-end sequence 204 to the subsequence 116(A) and hybridization of the 5'-end sequence 206 to the subsequence 116(B). DNA polymerase and DNA ligase repair the strand of the dsDNA 100 to which the second homologous repair template 202 is hybridized by creating new DNA 210. The second strand of the dsDNA 100 is then repaired using the first strand as a template.

The dsDNA 100 now includes the third target site 212 inserted into the middle of the second target site 116 (which is itself inserted in the middle of the first target site 102). The order of the subsequence 116(A) followed by the subsequence 212(A) encodes a second binary digit 214. This process can repeat to encode any number of binary digits 118, 214 within the dsDNA 100.

The encoding scheme described herein allows for insertion of DNA sequences representing an unbounded length of bits using only three different target sequences and six different homologous repair templates as explained below. The three target sequences are represented as $X_1X_2$, $Y_1Y_2$, and $Z_1Z_2$. The first portion of the target sequences (e.g., $X_1$, $Y_1$, or $Z_1$) corresponds to subsequence 102(A) or subsequence 116(A) shown in FIG. 1. The remaining portion of the target sequences (e.g., $X_2$, $Y_2$, or $Z_2$) corresponds to subsequence 102(B) or subsequence 116(B) shown in FIG. 1. Thus, each X, Y, and Z represents a DNA sequence of about 5 to 20 nucleotides such as, for example only, ACTGAA, GCCTCAT, TGACG, etc. In some implementations $X_1$=$X_2$, etc., but in other implementations the first portion of a target sequence may be different in sequence and/or length from the remaining portion of a target sequence.

The homologous repair templates all have end regions that are homologous to one of the target sequences. Thus, the homologous repair templates will have sequences of the structure: $X_1\_\_X_2$, $Y_1\_\_Y_2$, and $Z_1\_\_Z_2$. Recall that the middle region of the homologous repair templates itself encodes a target site. Thus, the middle region for any given homologous repair template will be one of $X_1X_2$, $Y_1Y_2$, or $Z_1Z_2$. In order to precisely control location of insertion, homologous repair templates do not encode the target site into which the homologous repair template is to be inserted. For example, $X_1X_1X_2X_2$ is not a valid homologous repair template according to this encoding. Thus, if the target sequence is "X" the middle region of the homologous repair template may encode the target sequence for "Y" or "Z"; if the target sequence is "Y" the middle region may encode "X" or "Z"; if the target sequence is "Z" the middle region may encode "X" or "Y". This leads to the six homologous repair templates: $X_1Y_1Y_2X_2$, $X_1Z_1Z_2X_2$, $Y_1X_1X_2Y_2$, $Y_1Z_1Z_2Y_2$, $Z_1X_1X_2Z_2$, and $Z_1Y_1Y_2Z_2$.

A context-dependent encoding using three target sites and six homologous repair templates is shown in Table 1 below. This is only one possible encoding and other encodings that use a greater number of target sites and homologous repair templates are also possible. Moreover, it is also possible to use multiple encodings in the same cell or system.

TABLE 1

Context-dependent binary encoding

| Current State | Repair Template | Encoded Bit |
|---|---|---|
| $X_1X_2$ | $X_1Y_1Y_2X_2$ | 0 |
| $X_1X_2$ | $X_1Z_1Z_2X_2$ | 1 |
| $Y_1Y_2$ | $Y_1X_1X_2Y_2$ | 0 |
| $Y_1Y_2$ | $Y_1Z_1Z_2Y_2$ | 1 |
| $Z_1Z_2$ | $Z_1X_1X_2Z_2$ | 0 |
| $Z_1Z_2$ | $Z_1Y_1Y_2Z_2$ | 1 |

The current state represents the sequence present in the dsDNA 100 at the time a given DSB is created. The current state may be tracked by a computer that is provided with a record of the initial target site 102 of the dsDNA 100 and with the sequences of each homologous repair template 106, 202 as the respective templates are brought into contact with the dsDNA 102. Thus, by referencing the current state as stored in the computer, the appropriate homologous repair template can be selected from Table 1 (or similar table for a different encoding) in order to encode the desired next bit.

Current state may also be recorded biochemically by using a genetically designed bi-stable switch. With one or more bi-stable switches, the current state may be recorded biochemically by creating molecular records based on which enzyme and/or homologous repair template was used last through a positive feedback loop. Recall the example encoding from above that makes it possible to encode any binary sequence through a combination of using three enzymes (i.e. one for each target site) and six homologous repair templates. In some implementations, genes encoding each of the enzymes and each of the homologous repair templates may also be present in the cell and each of the genes may be regulated by specific, and known promoters. The genes that makeup a given enzyme and accompany regulatory elements may be included in one or more operons. An operon is a contiguous region of DNA that includes cis-regulatory regions (repressors, promoters) and the coding regions for one or more genes or functional mRNAs (siRNA, tracrRNA, gRNA, shRNA, etc). The operon may be delivered in a circular vector or may be inserted into a linear chromosome. Activation of the genes by upregulation or cessation of suppression, may increase the amount of the desired enzyme and/or homologous repair template. This may also generate tracking molecules that can be used to monitor state. The tracking molecules may be part of the operons.

A "repressor" (and/or "knockdown") is a protein or mRNA (small hairpin loops (shRNA), interfering mRNA (RNAi or siRNA)) that binds to DNA/RNA and blocks either attachment of the promoter, blocks elongation of the polymerase during transcription, or blocks mRNA from translation.

The current level of a tracking molecule can serve as an on/off regulation signal for a gene encoding a given operon. In a system with a bi-stable repressor, the repressor has two states 0/1 which get flipped after each operation. For example, after the homologous repair template $X_1Y_1Y_2X_2$ is used (e.g., as identified by the concentration becoming greater than a threshold level) an associated tracking molecule may set the state of the bi-stable repressor. Continuing with this example, each of the homologous repair templates may be associated with a different bi-stable repressor and at any given time five of the bi-stable repressors may be in a state associated with "off" and the sixth may be in a state associated with "on." Thus, by examination of the state of multiple bi-stable repressors it is possible to identify which homologous repair template was used last. A similar mechanism may keep track of which enzyme was used last.

To avoid potential interference by molecules remaining from an earlier iteration, flipping of the bi-stable repressor may be handled as a multistage process that first pauses until editing of the dsDNA has stopped, then switches the state of the repressor using a temporally decaying signal indicating which state the repressor should change to. The temporally decaying signal is initiated during the active stage of the last iteration. Once the signal has decayed below a threshold level and the repressor has fully switched into the new state, operons regulating molecules used for the next iteration are unblocked. The operon that lacks the repressor appropriately corresponding to the current state and has a promoter for the current input signal is then able to proceed to transcribe.

A person having ordinary skill in the art will know how to create a bi-stable switch using proteins that serve as transcription factors or repressors having DNA-binding domains. A "transcription factor" is a protein that binds near the beginning of the coding sequence (transcription start site) for a gene or functional mRNA. Transcription factors are necessary for recruiting polymerase to transcribe DNA. Techniques for creating and using bi-stable molecular switches are described in Lebar, et al., *A bistable genetic switch based on designable DNA-binding domains*, 5 Nature Communications 5007 (2014).

One implementation of bi-stable switches is shown below in Table 2.

TABLE 2

| Bi-stable switch constructs | | | | | | |
|---|---|---|---|---|---|---|
| Prev State | Next Bit | Next State | Prev Symbol | Next Cut | Next Insert | Genetic Construct |
| R0 | 0 | R1 P0 | XX\|WW | X˜X\|W˜W | XYYX\|WYYW | R_P_R01 P10 X˜XT XYYX W˜WT WYYW |
| R1 | 0 | R0 P0 | YY\|ZZ | Y˜Y\|Z˜Z | YXXY\|ZXXZ | R_P_R10 P10 Y˜YT YXXY Z˜ZT ZXXZ |

TABLE 2-continued

Bi-stable switch constructs

| Prev State | Next Bit | Next State | Prev Symbol | Next Cut | Next Insert | Genetic Construct |
|---|---|---|---|---|---|---|
| R0 | 1 | R1 P0 | XX\|WW | X^X\|W^W | XZZX\|WZZW | R__P__R01 P10 X^XT XZZX W^WT WZZW |
| R1 | 1 | R0 P0 | YY\|ZZ | Y^Y\|Z^Z | YWWY\|ZWWZ | R__P__R10 P10 Y^YT YWWY Z^ZT ZWWYZ |

Repressor binding sites are represented by R_. Repressors bind in R1 but not in R0. Repressors blocks promoter. The promoter binding site is represented by P_. Promoter may be inducible with an additional signal that turns writing on/off completely. The agent that will toggle P from on to off is represented as P10. Depending on the specific implementation, P10 may be DNA, mRNA, or Protein. The agent that will toggle R from off to on is represented as R01. The agent that will toggle R from on to off is represented as R10. Depending on the specific implementation, both R01 and R10 may be DNA, mRNA, or Protein. The enzyme that cuts between $X_1X_2$ (or other target site) is represented by X^X (Y^Y or Z^Z). If the enzyme is the CRISPR/Cas9 system X^X represents the DNA/mRNA for gRNA that includes an X^X spacer. T represents tracrRNA that binds to Cas9.

The main difference from the previous chart is that there is an alphabet of four (X, Y, Z, W), but only need one previous state variable. This implementation may provide some efficiencies for encoding and engineering.

The current state is used to identify which enzyme 104, 200 is appropriate for creating a DSB in the dsDNA 102. The enzyme 104, 200 is brought into interaction with the dsDNA 100. For example, when the current state is $X_1X_2$ the selected enzyme is able to create a DSB in the $X_1X_2$ sequence. The following example in Table 3 shows how the binary values 010101 may be encoded in dsDNA 102 with the initial target sequence 102 of $X_1X_2$.

TABLE 3

Example of encoding binary values in DNA

| DNA Sequence | Encoded Binary Value |
|---|---|
| ... $X_1X_2$ ... | no value by itself |
| ... $X_1Y_1Y_2X_2$ ... | XY = 0; 0 |
| ... $X_1Y_1Z_1Z_2Y_2X_2$ ... | XY = 0; YZ = 1; 01 |
| ... $X_1Y_1Z_1X_1X_2Z_2Y_2X_2$ ... | XY = 0; YZ = 1; ZX = 0; 010 |
| ... $X_1Y_1Z_1X_1Z_1Z_2X_2Z_2Y_2X_2$ ... | XY = 0; YZ = 1; ZX = 0; XZ = 1; 0101 |
| ... $X_1Y_1Z_1X_1Z_1X_1X_2Z_2X_2Z_2Y_2X_2$ ... | ... ZX = 0; XZ = 1; ZX = 0; 01010 |
| ... $X_1Y_1Z_1X_1Z_1X_1Z_1Z_2X_2Z_2X_2Z_2Y_2X_2$ ... | ... XZ = 1; ZX = 0; XZ = 1; 010101 |

In one example implementation, using Cas9 with a PAM sequence of NNNNGATTT as the enzyme, the three target sites may be $X_1$ = TAGCCGTATCGAGCATCGATG | CGCNNNNGATT = $X_2$ $Y_1$ = GATCGATGGACTCTGCATCTA | TCGNNNNGATT = $Y_2$ $Z_1$ = CGGGACGATCGATCGGGCTAG | ACTNNNNGATT = $Z_2$ Where the PAM sequence is indicated by bold, $X_1$ is (SEQ ID NO: 1), $X_2$ is (SEQ ID NO: 2), $Y_1$ is (SEQ ID NO: 3), $Y_2$ is (SEQ ID NO: 4), $Z_1$ is (SEQ ID NO: 5), and $Z_2$ is (SEQ ID NO: 6). Note that each of $X_1$, $Y_1$, and $Z_1$ are 21 bp long.

Each of the target sites is recognized by a corresponding guide ssDNA that cuts the dsDNA at the location indicated by the "^" below. They should have a trans-activating crRNA (tracrRNA) that is a small trans-encoded RNA for attaching to Cas9 appended to the end. The respective ssDNA sequences are:

$gX_1$ = TAGCCGTATCGAGCATCGATG^CGC (SEQ ID NO: 1)

$gY_1$ = GATCGATGGACTCTGCATCTA^TCG (SEQ ID NO: 3)

$gZ_1$ = CGGGACGATCGATCGGGCTAG^ACT (SEQ ID NO: 5)

Then a homology directed repair sequences of $X_1Y_1Y_2X_2$ is: TAGCCGTATCGAGCATCGATG|GATCGATGGACTCT-GCATCTA|TCGNNNNGATT|CGCNNNNGATT (SEQ ID NO: 7) and a homology directed repair sequences of $Y_1X_1X_2Y_2$ is: GATCGATGGACTCTGCATCTA|TAGCCGTATCGAG-CATCGATG|CGCNNNNGATT|TCGNNNNGATT (SEQ ID NO: 8). Other homology directed repair sequences can be designed according to the same pattern.

An initial cut of the target site $X_1X_2$ will create a DSB that appears as (only one strand of the dsDNA is shown):

. . . TAGCCGTATCGAGCATCGATG   CGCNNNNG-ATT . . . (SEQ ID NOs: 1 and 2)

After HDR with $X_1Y_1Y_2X_2$, one strand of the dsDNA will have the following sequence which now includes the target site $Y_1Y_2$ indicated by italics:

(SEQ ID NO: 7)
...TAGCCGTATCGAGCATCGATG|*GATCGATGGACTCTGCATCTA*||
*TCG*NNNNGATT|CGCNNNNGATT....

The dsDNA is now able to be cut by a Cas9 that has g $Y_1$ creating a DSB at the location represented by "||". HDR may be performed with $Y_1X_1X_2Y_2$, for example, further adding to the dsDNA and completing another iteration of encoding. This may be continued with various sequences of cuts and homologous repair templates to encode any series of bits.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations may be modified or omitted.

Figure 3:
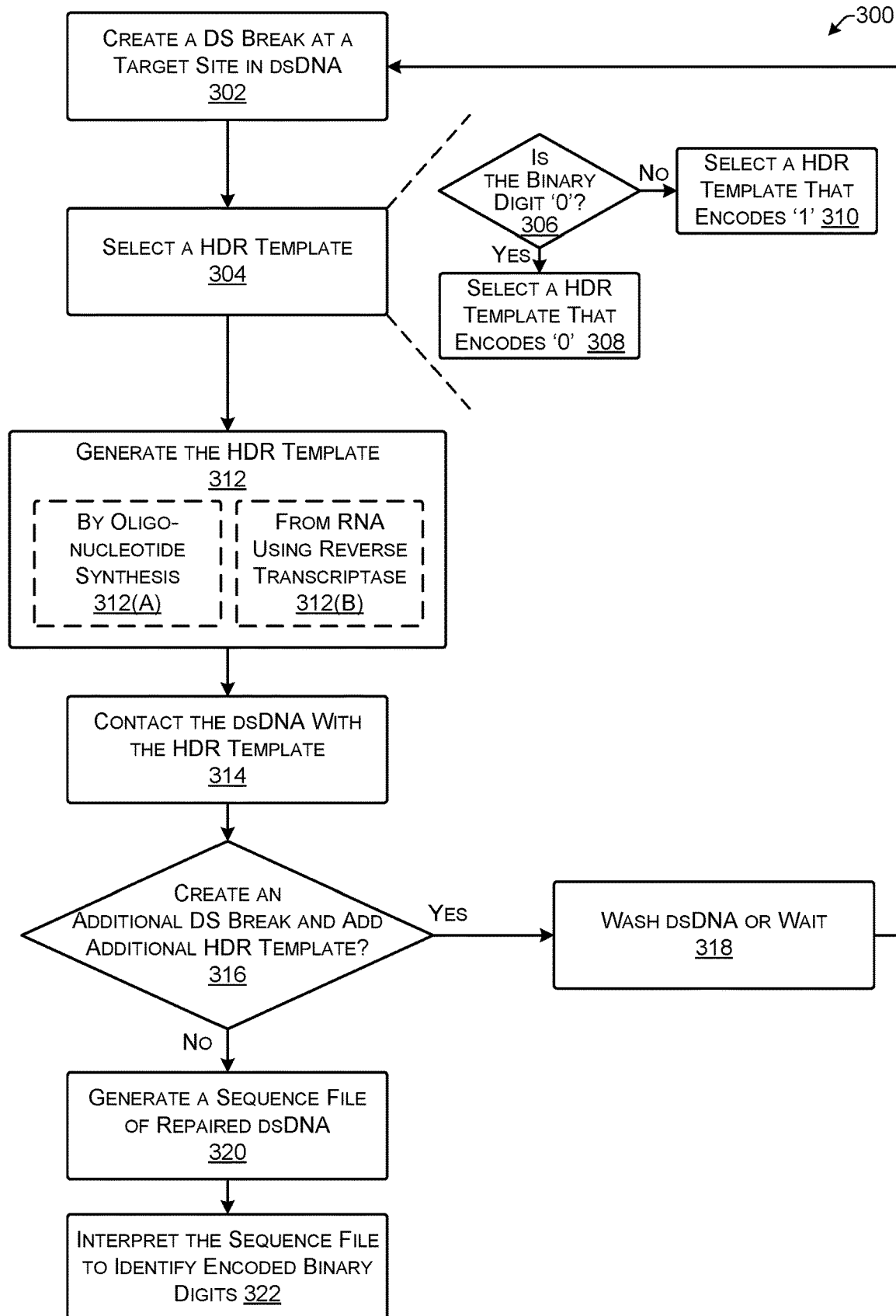
FIG. 3 shows an illustrative process for cutting dsDNA, inserting DNA through homology directed repair, and sequencing the DNA to identify the encoded binary data.

FIG. 3 shows process 300 for iteratively adding DNA to the site of a DSB in a dsDNA molecule. The process 300 corresponds in part to the schematics shown in FIGS. 1 and 2.

At 302, a first DSB is created at a first target site 102 in the dsDNA 100 with a first enzyme 104. In order to limit where the first enzyme 104 cuts the dsDNA 100, the first target site 102 may be unique in the dsDNA at the time of making the first DSB. The first target site 102 may also be unique across a population of dsDNA that is available for the first enzyme to act on. For example, if there are multiple circular dsDNA molecules within a cell, the first target site 102 may exist only once within the entire population of circular dsDNA molecules. Alternatively, the first target site 102 may be unique per dsDNA molecule, but the first enzyme 104 may have access to multiple different dsDNA molecules each including one instance of the first target site 102. It is understood by persons having ordinary skill in the art that the enzyme (even if referred to in the singular herein) may include a plurality of individual and equivalent enzyme molecules. In some implementations, the first target site 102 may include a first subsequence 102(A) that is repeated once resulting in a second subsequence 102(B) that is the same as the first subsequence 102(A). For example, if the first subsequence 102(A) is GTACTA then the second subsequence 102(B) is the same and the sequence of the target site 102 is GTACTAGTACTA (SEQ ID NO: 9).

The first enzyme 104 may be any of the illustrative types of enzymes identified above such as a restriction enzyme, HE, a CRISPER/Cas system, a TALEN, or a zinc finger.

At 304, a first homologous repair template 106 to encode a first binary digit 118 is selected. Given the binary digit 118 to encode according to an encoding scheme, the identity of the first target site 102 is used to select the first homologous repair template 106. The homologous repair template 106 may include a 3'-end sequence and a 5'-end sequence each encoding a second subsequence that is complementary to the first subsequence 102(A), 102(B) in the first target site 102. Thus, in this implementation the 3'-end sequence 108 and the 5'-end sequence 110 have the same sequence, but in other implementations they may have different sequences. The first homologous repair template 106 may also include a middle portion that includes two adjacent instances of a third subsequence 112(A), 112(B) that forms the next target site after insertion into the dsDNA.

As mentioned above, selecting the homologous repair template 106 may be based on an encoding scheme such as that shown in Table 1 above.

At 306, it is determined if the next digit is 0. Being a binary system this is functionally equivalent to determining if the next digit is not 1. If the next digit to be encoded is a 0, the process 300 proceeds to 308 and selects a homologous repair template 106 that when inserted into the target site 102 encodes a 0. If the next binary digit is not 0, thus being 1, process 300 proceeds to 310 and selects a homologous repair template 106 that when inserted into the target site 102 encodes a 1. The appropriate binary digit 118 is represented by the partial sequence 112(A) of the target site 102 followed by the partial sequence 116(A) of the homologous repair template 106.

At 312 the homologous repair template 106 is generated. The homologous repair template 106 may be generated at 312(A) artificially by an oligonucleotide synthesizer. Oligonucleotide synthesizers are discussed in more detail below.

At 312(B) the homologous repair temple 106 may be generated by a gene under control of a regulated promoter. The mRNA gene product may be converted to DNA through use of reverse transcriptase to create a DNA molecule that is the final homologous repair template 106. In some implementations the mRNA may itself serve as a homology repair template without the need to convert to DNA first. Rafael Yáñez-Muñoz, See *RNA to repair DNA—what next*??, British Society for Gene and Cell Therapy (Jan. 14, 2015) Available on-line at www.bsgct.org/rna-to-repair-dna-what-next/; Keskin, H., Shen., Y. et al. *Transcript-RNA-templated DNA recombination and repair.* 515 Nature 436-439 (2014); and Storici, F., Bebenek, K. et al., RNA-templated DNA repair. 447 Nature 338-341(2007).

At 314 the dsDNA 100 is contacted with the first homologous repair template 106. Contacting the dsDNA 100 with the first homologous repair template 106 may involve adding or moving multiple copies of the first homologous repair template 106 into a chamber that contains the dsDNA 100 such as, for example, by a microfluidics system. In one implementation, contacting the dsDNA 100 involves upregulating expression of a gene encoding for a RNA sequence that is itself the homologous repair template 106 or that serves as a template for creation of the homologous repair template 106. Upregulating expression of the gene may include any of activating a promoter controlling transcription of the gene and/or inhibiting action of a repressor.

Typically, this contacting occurs in an environment with multiple copies of the dsDNA 100 and multiple copies of the homologous repair template 106. There may be hundreds, thousands, or more copies of each of the dsDNA 100 and the homologous repair template 106. After contacting the dsDNA 100 with the homologous repair template 106 there will be a subset of the original dsDNA 100 and homologous repair templates 106 that successfully perform homology directed repair to add the middle portion of the homologous repair template 106 to the dsDNA 100. There will also be a different subset of the dsDNA 100 that is not repaired or is repaired other than by incorporating the middle portion of the homologous repair template 106. Discussions herein may describe the dsDNA 100 as if every molecule is successfully repaired by the homologous repair template 106, but persons of ordinary skill in the art will understand that only a subset of a population of dsDNA molecules are repaired in this way.

At 316, it is determined if an additional DSB is to be created in the dsDNA 100 and HDR performed with a second homologous repair template 202. If yes because, for example, another binary digit is to be encoded in the dsDNA 100, process 300 proceeds along the "yes" path to 318.

At 318, the dsDNA 100 may be treated to remove or inactivate any of the first enzyme 104 and/or the first homologous repair template 106 that remain. This reduces the potential for enzyme or homologous repair template remaining from an earlier iteration creating an unintended cut or HDR in a later iteration. In one implementation, such as a cell-free microfluidics system, the dsDNA 100 may be washed to remove the first enzyme and/or the first homologous repair template. In one implementation, there may be a waiting time of sufficient length for concentration of the first enzyme or the first homologous repair template to decrease below a threshold level. The threshold level may be a level at which minor or substantially no enzyme/homologous repair template activity occurs. The threshold level may be identified by experimentation. Natural degradation processes in a cell may cause enzymes and free ssDNA or ssRNA to degrade over time. The degradation speed may be increased by addition of proteasomes or nucleases. Homologous repair templates may also be made inactive by addition of complementary ssDNA sequences that anneal to the homologous repair templates creating dsDNA and preventing the homologous repair templates from invading the dsDNA with a DSB.

If no additional DSB is to be created at 316, a sequence file of repaired dsDNA is generated at 320, and the sequence file is interpreted at 322 to identify encoded binary digits.

Figure 4:
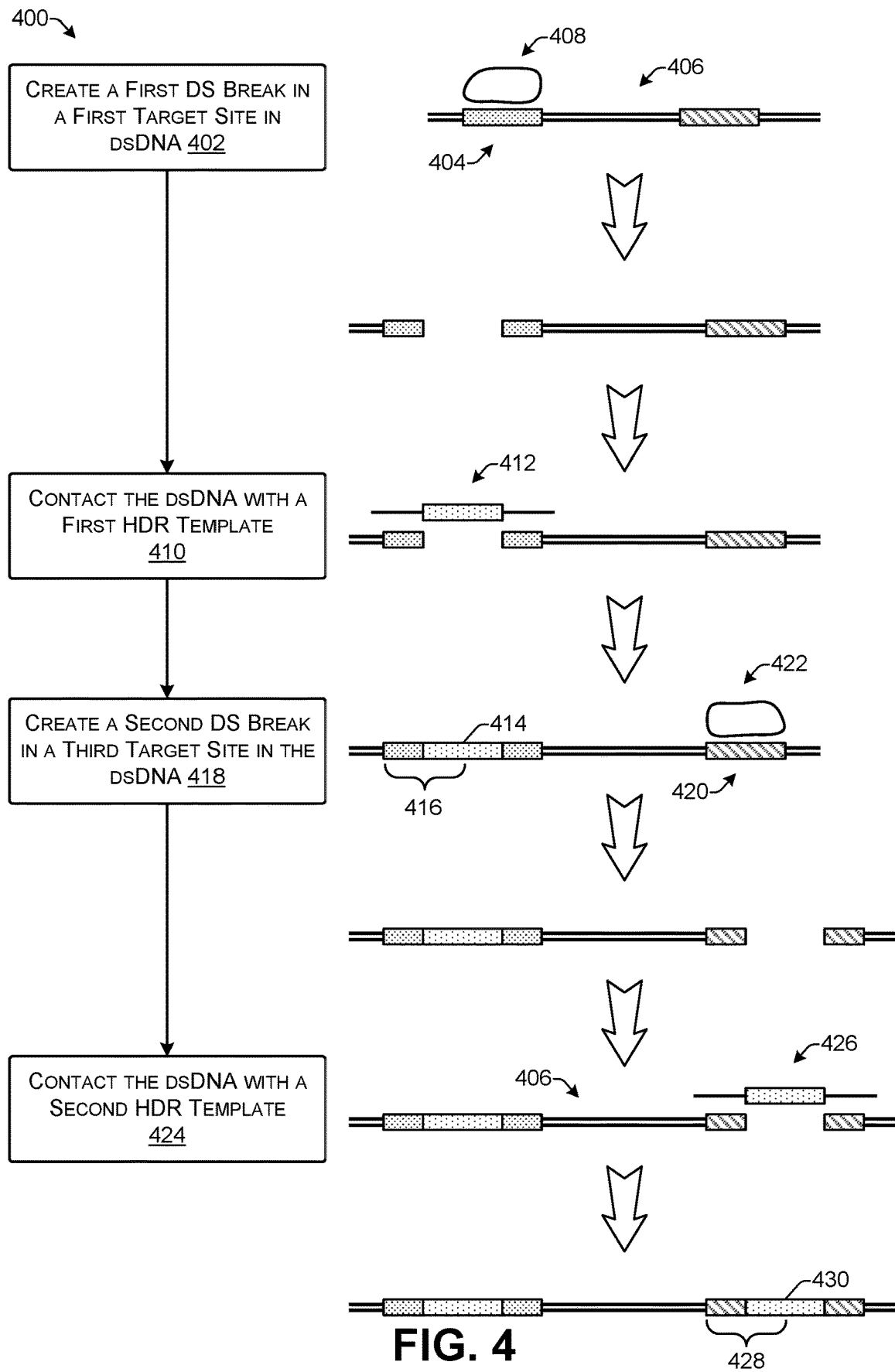
FIG. 4 shows an illustrative process for inserting DNA into two locations in dsDNA according to two different encoding schemes.

FIG. 4 shows a process 400 of adding DNA at two different target sites in dsDNA according to two different encodings. Two different encodings using fully orthogonal components allow for writing two different binary strings in the same dsDNA without cross talk. If two different encodings are fully orthogonal, the enzymes used to make DSBs for the first encoding will recognize target sites different from the target sites recognized by the enzymes used for the second encoding. Similarly, the target sites sequences for the first encoding will be sufficiently different from the target site sequences for the second encoding such that there is no hybridization between homologous repair templates for one encoding and DNA flanking DSBs associated with the other encoding. Use of two different encodings also allows for encoding the same binary sequence with redundancy. Although only two different encodings are described herein, it is to be understood that this technique may be equally applicable to any number of different encodings.

The process 400 is illustrated by a schematic showing dsDNA manipulations. The accompanying schematic uses representations similar to those shown in FIG. 1 and FIG. 2. Unless described otherwise, features of FIG. 4 have the same or similar functions to visually similar features in FIG. 1 and FIG. 2.

At 402, a first DSB is created in a first target site 404 in dsDNA 406 with a first enzyme 408. The first enzyme 408 may be any of the type of enzymes capable of creating DSBs in dsDNA described above. The dsDNA 406 may be linear DNA or circular DNA. In one implementation, the dsDNA 406 may be a circular DNA molecule present in a cell-free system.

At 410, the dsDNA 406 is contacted with the first homologous repair template 412. The first homologous repair template 412 includes a 3'-end sequence that is complementary to a first portion of the first target site 404 and a 5'-end sequence that is complementary to a second portion of the first target site 404. Some portion of a population of the dsDNA 406 that is brought into contact with a population of the first homologous repair templates 412 will undergo HDR and incorporate a middle portion of the first homologous repair template into the dsDNA 406. The middle portion of the homologous repair template 412 includes the sequence that is between the 3'-end sequence and the 5'-end sequence. In a cell-free implementation, the contacting may be performed in part by a microfluidic mechanism moving the first homologous repair template 412 into a same chamber as the dsDNA 406 so that the first homologous repair template 412 may hybridize to one strand of the dsDNA 406.

Once integrated into the dsDNA 406 by the operation of DNA polymerase and DNA ligase, a portion of the target site 404 is located adjacent to the dsDNA 414 generated by repair of the first DSB with the first homologous repair template 412. The order of these two DNA sequences encodes a first binary digit 416 according to a first encoding scheme. The DNA sequence generated by repair with the first homologous repair template 412 is itself a second target site 414 according to the first encoding scheme. Thus far, process 400 is similar to the DNA manipulation shown in FIG. 1.

At 418, a second DSB is created in a third target site 420 with a second enzyme 422. The third target site 420 belongs to a different encoding than the first target site 404 or the second target site 414. Thus, to prevent cross talk between the two different encodings, the third target site 420 has a sequence that is different than the first target site 404 and different than the second target site 416. The third target site 420 does not overlap the first target site 404. Because it does not overlap the first target site 404, the third target site 420 is at least one base pair removed from the first target site 404. The second enzyme 422 recognizes the second target site 414, but does not recognize or cut the first target site 404. The first enzyme 408 and the second enzyme 422 may be the same type of enzyme (e.g., both CRISPER/Cas) or they may be different types of enzymes (e.g., one restriction enzyme and one TALEN).

At 424, the dsDNA 406 is contacted with a second homologous repair template 426. The second homologous repair template 426 also includes a 3'-end sequence which is complementary to a first portion of the third target site 420 and a 5'-end sequence which is complementary to a second portion of the third target site 420. Following repair of the second DSB with the second homologous repair template 426, a sequence of a portion of the third target site 420 adjacent to a portion of the dsDNA generated by repairing the second DSB encodes a second binary digit 428 according to a second encoding scheme. The DNA sequence complementary to a middle portion of the second homologous repair template 426 comprises a fourth target site 430 according to the second encoding scheme. The fourth target site 430 is different from the third target site 420 and also different from either of the target sites for the first encoding (i.e., the first target site 404 and the second target site 414).

At this point a DSB has been created and repaired with a homologous repair template according to the first encoding and a different DSB has been created and repaired with a different homologous repair template according to the second encoding. Thus, the dsDNA 406 includes a first binary digit 416 according to the first encoding and a second binary digit 428 according to the second encoding. This process of creating DSBs and repairing the breaks with a homologous repair template may be repeated iteratively according to either of the first or the second encodings. In some implementations, the encodings may be alternated, or interleaved, so that a binary digit is added according to the first encoding then a binary digit is added according to the second encoding and so on.

Illustrative Cellular Implementation Environment

Figure 5:
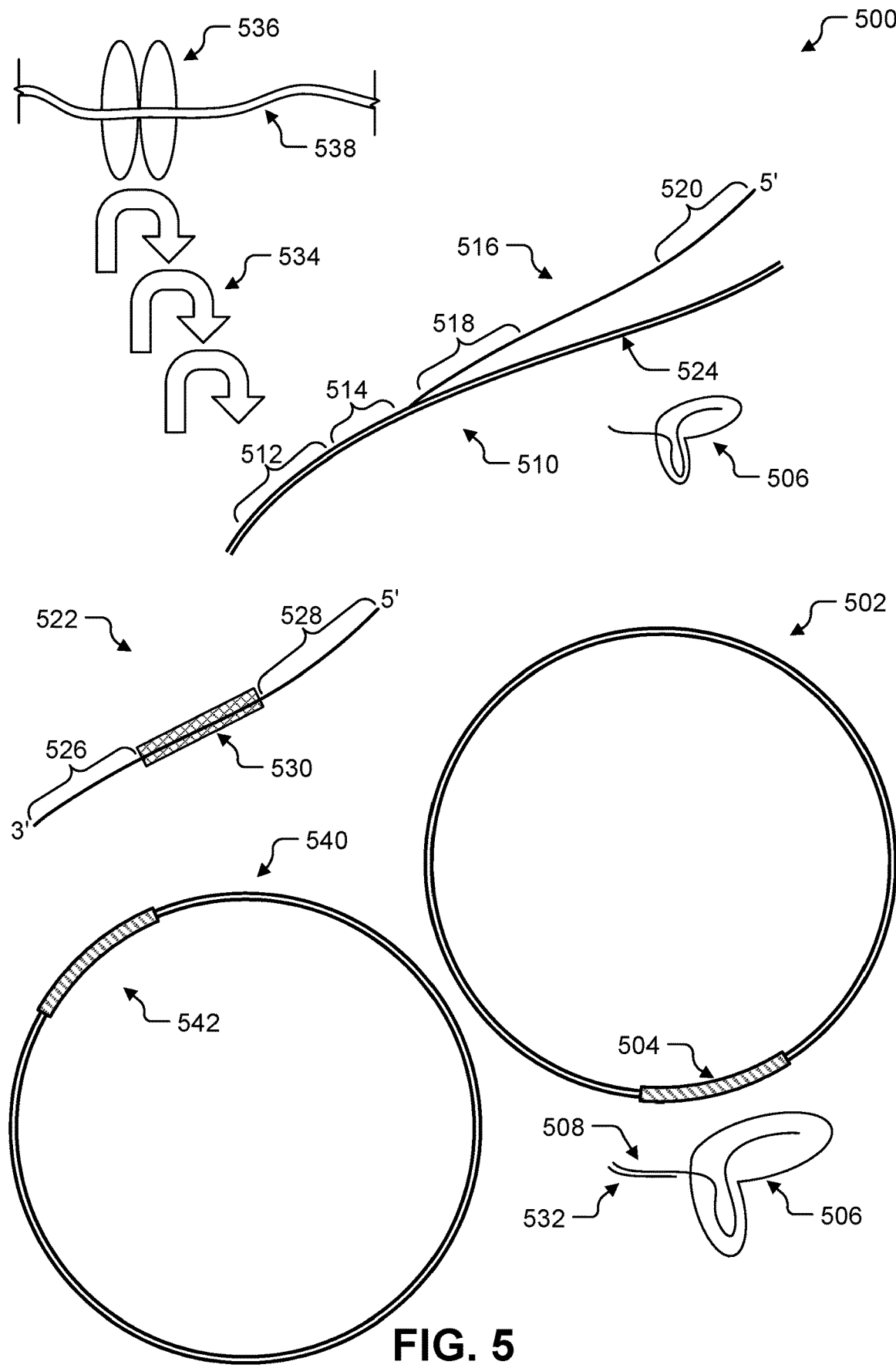
FIG. 5 show illustrative components of a cell for inserting new DNA into existing DNA.

FIG. 5 shows an illustrative cell 500 that is capable of heritability storing binary data. The cell 500 may be an *E. coli* cell, a *Saccharomyces cerevisiae* cell, or a cell from another single-celled organism. It may also be a cell from a multi-cellular organism grown in culture. The cell 500 may contain a dsDNA molecule 502 that has a first target site 504. The cell 500 may also contain a first enzyme 506 that is configured to create a DSB within the first target site 504. For example, the first enzyme 506 may be a CRISPR/Cas system comprising a gRNA 508 that includes a spacer region complementary to one strand of the dsDNA 502 at the first target site 504.

The cell 500 may also include a gene 510 under the control of a promoter 512 and an operator 514. A promoter is a region of DNA that initiates transcription of a particular gene. Promoters are located near the transcription start sites of genes, on the same strand and upstream on the DNA (towards the 5' region of the sense strand). An operator is a segment of DNA to which a transcription factor binds to regulate gene expression. The transcription factor is a repressor, which can bind to the operator to prevent transcription.

The gene 510 may encode a ssRNA sequence 516 comprising a 3'-end sequence 518 and a 5'-end sequence 520. A homologous repair template 522 may be generated from the gene 510. In one implementation, the homologous repair template 522 is the ssRNA sequence 516 itself. The 3'-end sequence 518 and the 5'-end sequence 520 are complementary to one strand of the dsDNA molecule 502 over at least part of the first target site 504. Homology between the 3'-end sequence 518 and the 5'-end sequence 520 allows the ssRNA sequence 516 to hybridize with portions of the dsDNA 502 on either side of a DSB created in the first target site 504.

In implementations in which the gene 510 directly encodes the homologous repair template 522, the gene 510 will encode a target site 524 that may be cut by an enzyme such as the first enzyme 506. Unless protected from the enzyme, the target site 524 in the gene 510 may be unintentionally cut when the enzyme is introduced.

One technique for protecting the target site 524 from the first enzyme 506 is physical separation. In a cell-free system, such as one that uses microfluidics, the gene 510 may be maintained in one chamber and the ssRNA sequence 516 may be moved from the chamber containing the gene 510 into a different chamber where the enzyme is introduced.

Physical separation may also be used in cellular implementations. The gene 510 and the enzyme may be contained in different cellular chambers. In one implementation, the gene 510 may be in the nucleus and the enzyme may be outside the nucleus in the cytoplasm or in another cellular chamber. The gene 510 may remain in the nucleus if it is part of the cell's genome. A nuclear export signal may be used to keep the enzyme out of the nucleus. A nuclear export signal (NES) is a short amino acid sequence of 4 hydrophobic residues in a protein that targets it for export from the cell nucleus to the cytoplasm through the nuclear pore complex using nuclear transport. Persons of ordinary skill in the art will be able to modify or engineer the enzyme to include a NES.

The ssRNA sequence 516 may be exported from its site of transcription in the nucleus to the cytoplasm or other destination outside the nucleus where the enzyme is present. RNA export is described in Sean Carmody and Susan Wente, *mRNA Nuclear Export at a Glance*, 122 J. of Cell Sci. 1933-1937 (2009) and Alwin Köhler and Ed Hurt, *Exporting RNA from the Nucleus to the Cytoplasm*, 8 Nature Reviews Molecular Cell Biology 761-773 (2007).

In one implementation, the gene 510 may include a sequence with a portion that is later removed by splicing. This additional portion will prevent the enzyme from recognizing a target site 524, but the ssRNA sequence 516 will not become a homologous repair template 522 until the splice site is removed. There are multiple types of alternative splicing, of which the is exon skipping. Exon skipping is one way to cause splicing in the ssRNA sequence 516; in this case, an exon may be spliced out of the primary transcript. Persons having ordinary skill in the art will understand how to design the gene 510 so that it includes a splice site at a specified location. Alternative splicing may be implemented even if the gene 510 and enzyme are not physically separated.

Self-excising elements may function similarly to splicing. The gene 510 may be designed to include region that when transcribed in to RNA includes one or more self-excising elements. The self-excising elements prevent the gene 510 from being recognized by the enzyme and the excision coverts the ssRNA sequence 516 into the homologous repair template 522. One type of self-excising elements are ribozymes, which are RNA enzymes that function as reaction catalysts. So ribozymes are just RNA sequences that catalyze a (transesterification) reaction to remove itself from the rest of the RNA sequence. Essentially these are considered introns, which are intragenic regions spliced from mRNA to produce mature RNA with a continuous exon (coding region) sequence. Self-excising introns/ribozymes consist of type I and II introns. They are considered self-splicing because they do not require proteins to initialize the reaction. Self-excising sequences are known and one of ordinary skill in the art will understand how to include a self-excising sequence in the gene 510. Aspects of self-excising ribozymes are shown in Internet domain 2011.igem.org/Team:Waterloo.

A series of homologous bridges may also be used to generate a recombinant sequence that is the gene template for the ssRNA sequence 516. The homologous bridges may be present in the DNA at various, separate locations so that the gene 510 does not include a target site 524. This technique is also known as multi-fragment cloning or extension cloning. The final homologous repair template 522 is made up of transcripts of the multiple overlapping segments. One suitable technique for combining the multiple-overlapping fragments into the homologous repair template 522 is Sequence and Ligation-Independent Cloning (SLIC). Mamie Li and Stephen Elledge, *Harnessing Homologous Recombination in vitro to Generate Recombinant DNA Via SLIC*, 4 Nature Methods 250-256 (2007). Another suitable technique for joining multiple-overlapping fragments is provided by Jiayuan Quan and Jingdong Tian, *Circular Polymerase Extension of Cloning of Complex Gene Libraries and Pathways*, 4(7) PLoS ONE (2009).

In one implementation, the homologous repair template 522 is a ssDNA sequence complementary to the ssRNA sequence 516. The ssDNA sequence may be created by reverse transcriptase reading the ssRNA sequence 516 and synthesizing a complementary ssDNA sequence. Reverse transcriptase (RT) is an enzyme used to generate complementary DNA (cDNA) from an RNA template, a process termed reverse transcription. RT is widely used in the laboratory to convert RNA to DNA for use in procedures such as molecular cloning, RNA sequencing, polymerase chain reaction (PCR), and genome analysis. RT enzymes are widely available from multiple commercial sources.

The 3'-end sequence 526 and the 5'-end sequence 528 of the homologous repair template 522 are complementary to one strand of the dsDNA 502 over at least a portion of the first target site 504. The homologous repair template 522, in both ssDNA and ssRNA implementations, includes a middle portion 530 that, when incorporated into the dsDNA 502, forms a target site as described above in this disclosure.

Enzyme 506 is illustrated here as a CRISPR/Cas complex with gRNA 508. Other types of enzymes discussed above may be used instead of the CRISPR/Cas complex. The single-stranded tail of the gRNA 508 may be extended with a sequence complementary to all or part of the homologous repair template 522. The homologous repair template 522 may bind to the tail of the gRNA 508 forming a double-stranded region 532. This brings a copy of the homologous repair template 522 into close proximity with the location of the DSB created by the CRISPR/Cas complex 506.

The extended tail of the gRNA 508 may also be designed so that it matches the binding domain of a transcription activator-like effector (TALE) protein. The TALE protein may also have a binding domain complementary to the homologous repair template 522. This will also bring the homologous repair template into close proximity with the location of the DSB. The tail of the gRNA 508 may be extended to create regions for attachment of multiple copies of the homologous repair template 522 or TALE proteins.

TALE proteins are proteins secreted by *Xanthomonas* bacteria via their type III secretion system when they infect various plant species. These proteins can bind promoter sequences in the host plant and activate the expression of plant genes that aid bacterial infection. They recognize plant DNA sequences through a central repeat domain consisting of a variable number of about 34 amino acid repeats. There appears to be a one-to-one correspondence between the identity of two critical amino acids in each repeat and each DNA base in the target sequence. The most distinctive characteristic of TAL effectors is a central repeat domain containing between 1.5 and 33.5 repeats that are usually 34 residues in length (the C-terminal repeat is generally shorter and referred to as a "half repeat"). A typical repeat sequence may be shared across many TALE proteins but the residues at the 12th and 13th positions are hypervariable (these two amino acids are also known as the repeat variable diresidue or RVD). This simple correspondence between amino acids in TAL effectors and DNA bases in their target sites makes them useful for protein engineering applications.

Subsequent to creation of a DSB in the target site 504, the molecule 532 that has hybridized to the tail of the gRNA 508 may be released. In some implementations, introduction of a nucleotide sequence complementary to the tail of the gRNA 508 or binding domain of the TALE protein may compete with the homologous repair template 522 and cause disassociation of the homologous repair template 522. This competition may cause the homologous repair template 522 to become available for binding to the dsDNA 502 on either side of the DSB.

The cell 500 may also include one or more engineered signaling pathways 534. As used herein, "engineered signaling pathway" includes any pathway in which at least one portion of the pathway is intentionally modified with molecular biology techniques to be different from the wild type pathway and a signal (intracellular or extracellular) causes a change in a rate of transcription of a gene. The engineered signaling pathway 534 may induce a promoter such as the promoter 512 described above. The engineered signaling pathway 534 may also cause a transcription factor to bind to an operator such as the operator 514 described above and prevent transcription. In one implementation, the gene affected by the engineered signaling pathway 534 may be the gene 510 that encodes for the ssRNA sequence 516. Thus, the engineered signaling pathway 534 may function to control an amount of the homologous repair template 522 available in the cell 500. In one implementation, the gene affected by the engineered signaling pathway 534 may encode for an enzyme that creates DSBs in dsDNA such as enzyme 506. Thus, the number of enzymes which create DSBs in the target sequences 504 may be regulated by the engineered signaling pathway 534.

The cell 500 may include multiple different engineered signaling pathways 534 each responding to a unique signal and each promoting or repressing expression of genes responsible for the creation of the homologous repair templates 522 and/or enzymes 506. Thus, intracellular or extracellular signals may be used to vary the levels of homologous repair templates 522 and/or enzymes 506 in the cell 500 thereby changing which target sequences 504 are cut and which sequences are used to repair DSBs through HDR. By engineering signaling pathways that affect the availability of homologous repair templates 522 and/or enzymes 506, cells might be modified to include a control system for encoding arbitrary sequences of binary data in dsDNA 502 of the cell 500 according to the encoding techniques described above.

In one implementation, the engineered signaling pathway 534 may include an external receptor 536 that can detect extracellular signals across a membrane 538. The membrane 538 may be a cell wall, lipid bilayer, or artificial cell wall. In one implementation, the external receptor 536 may be a G protein-coupled receptor (GPCR). GPCRs constitute a large protein family of receptors, that sense molecules outside the cell 500 and activate inside signal transduction pathways 534 and, ultimately, cellular responses. The GPCR is activated by an external signal in the form of a ligand or other signal mediator. This creates a conformational change in the GPCR, causing activation of a G protein. Further effect depends on the type of G protein. G proteins are subsequently inactivated by GTPase activating proteins, known as RGS proteins. The ligands that bind and activate these GPCRs include light-sensitive compounds, odors, pheromones, hormones, and neurotransmitters, and vary in size from small molecules to peptides to large proteins. When a ligand binds to the GPCR it causes a conformational change in the GPCR, which allows it to act as a guanine nucleotide exchange factor (GEF). The GPCR can then activate an associated G protein by exchanging its bound GDP for a GTP. The G protein's $\alpha$ subunit, together with the bound GTP, can then dissociate from the $\beta$ and $\gamma$ subunits to further affect intracellular signaling proteins or target functional proteins directly depending on the a subunit type.

In one implementation, the external receptor 536 may be a photosensitive membrane protein. Photoreceptor proteins are light-sensitive proteins involved in the sensing and response to light in a variety of organisms. Photoreceptor proteins typically consist of a protein moiety and a non-protein photopigment that reacts to light via photoisomerization or photoreduction, thus initiating a change of the receptor protein which triggers a signal transduction cascade. Pigments found in photoreceptors include retinal (retinylidene proteins, for example rhodopsin in animals), flavin (flavoproteins, for example cryptochrome in plants and animals) and bilin (biliproteins, for example phytochrome in plants). One example of engineered use of light-sensitive proteins is found in Alvin Tamsir et al., *Robust Multicellular Computing Using Genetically Encoded NOR Gates and Chemical 'Wires'*, 469 Nature 212-215 (2011).

The external receptor 536, in some implementations, may also be a membrane-bound immunoglobulin (mIg). A membrane-bound immunoglobulin is the membrane-bound form of an antibody. Membrane-bound immunoglobulins are composed of surface-bound IgD or IgM antibodies and associated Ig-$\alpha$ and Ig-$\beta$ heterodimers, which are capable of signal transduction through a signaling pathway 534 in response to activation by an antigen.

In one implementation, temperature may activate the engineered signaling pathway 534. Thus, by altering the temperature of the cell 500, genes controlling things such as homologous repair templates or enzyme synthesis may be up or down regulated. Temperature sensing molecules that naturally occur in single celled organisms include heat shock proteins and certain RNA regulatory molecules, such as riboswitches. Heat shock proteins are proteins that are involved in the cellular response to stress. One example of a heat shock protein that responds to temperature is the bacterial protein DnaK. Temperatures elevated above normal physiological range can cause DnaK expression to become up-regulated. DnaK and other heat shock proteins can be utilized for engineered pathways that respond to temperature. Riboswitches are a type of RNA molecule that can respond to temperature in order to regulate protein translation. An example of a temperature-regulated engineered pathway that has utilized a riboswitch can be found in Neupert, J, et al., Nucleic Acids Res, 2008, 36(19):e124. Another example of a temperature-sensitive molecule that can be utilized to regulate engineered cell pathways is a temperature-sensitive mutant protein. Single mutations can be made to proteins, which cause the proteins to become unstable at high temperatures, yet remain functional at lower temperatures. Methods for synthesizing temperature-sensitive mutant proteins can be found in Ben-Aroya, S, et al., Methods Enzymol, 2010, 470, 181-204. An example of a temperature-controlled engineered pathway that utilizes a temperature-sensitive mutant can be found in Hussain, F, et al., 2014, PNAS, 11(3), 972-977.

In one implementation, ion concentration or pH may activate the engineered signaling pathway 534. With engineered signaling pathways 534 of this type, placing the cell 500 in a different ionic environment or altering pH surrounding the cell 500 may be used to control the availability of a given homologous repair template or enzyme. Examples of cellular sensing molecular mechanisms that detect ionic strength or pH include many viral proteins, such as herpes simplex virus gB, rubella virus envelope protein, influenza hemagglutinin, and vesicular stomatitis virus glycoprotein. An example of a natural cellular pathway that is regulated by pH is penicillin production by *Aspergillus nidulans* (Espeso, E, et al., 1993, EMBO J, 12(10), 3947-3956). Another example of a pH-sensitive molecule that can be utilized to regulate engineered cell pathways is a pH-sensitive mutant protein. Single mutations can be made to proteins, which can cause the proteins to become less stable in either acidic or basic conditions. For example, pH-sensitive antibodies can bind to an antigen at an optimal pH, but are unable to bind to an antigen at a non-optimal pH. A technique for creating pH-sensitive antibodies that can be used for engineered signaling pathways can be found in Schroter, C, et al., 2015, MAbs, 7(1), 138-51. These and other similar sensing mechanisms may be engineered to affect the behavior of a promoter 512 or operator 514

The cell 500 may also include an additional dsDNA molecule 540 that also includes a target site 542. Similar to the first dsDNA molecule 502, the additional dsDNA molecule 540 may include only a single instance of the target site 542. Or, the additional dsDNA molecule 540 may include multiple copies of the same target site or multiple different target sites.

The additional dsDNA molecule 540 and the target site 542 may have identical or similar sequences to the first dsDNA molecule 502 and the first target site 504. Thus, the additional dsDNA molecule 540 may be thought of as a "copy" of the first dsDNA molecule 502. This additional copy of an identical or similar molecule may provide redundancy by creating a second string of binary data that, absent errors, will record the same series of 0s and 1s in both dsDNA molecules 502, 540. In one implementation, the additional dsDNA molecule 540 may include a target site 542 with a different sequence than target site 504 in the first dsDNA molecule 502. Having different target sites 504, 542 in different dsDNA molecules 502, 540 allows for simultaneous, or alternating, encoding of binary data in two different encoding schemes. The two different encoding schemes may be non-overlapping or "orthogonal" so that the enzymes and homologous repair templates associated with one encoding scheme do not interact with the dsDNA molecule used for the other encoding scheme. It is understood, that in actual implementation there may be many hundreds of thousands of dsDNA molecules with respective target sites. There may also be a corresponding number of different encoding schemes and different sequences for the respective target sites.

Illustrative System and Computing Devices

Figure 6:
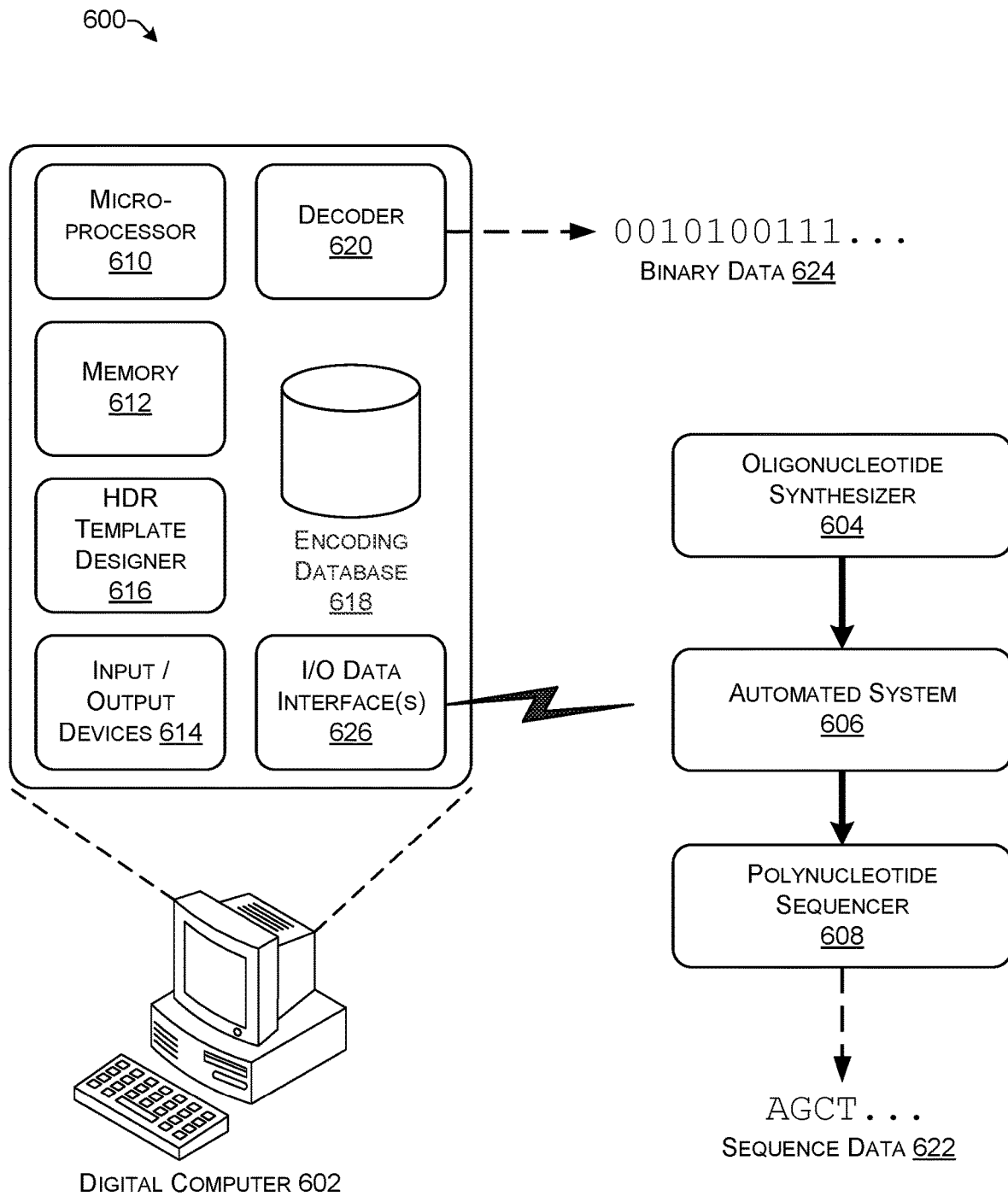
FIG. 6 shows an illustrative system for implementing features of this disclosure.

FIG. 6 shows an illustrative architecture 600 for implementing and interacting with DNA molecules storing data introduced through HDR as described above. The architecture may include any of a digital computer 602, an oligonucleotide synthesizer 604, an automated system 606, and/or a polynucleotide sequencer 608. The architecture 600 may also include other components besides those discussed herein.

As used herein, "digital computer" means a computing device including at least one hardware microprocessor 610 and memory 612 capable of storing information in a binary format. The digital computer 602 may be a supercomputer, a server, a desktop computer, a notebook computer, a tablet computer, a game console, a mobile computer, a smartphone, or the like. The hardware microprocessor 610 may be implemented in any suitable type of processor such as a single core processor, a multicore processor, a central processing unit (CPU), a graphical processing unit (GPU), or the like. The memory 612 may include removable storage, non-removable storage, local storage, and/or remote storage to provide storage of computer readable instructions, data structures, program modules, and other data. The memory 612 may be implemented as computer-readable media. Computer-readable media includes, at least, two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

The digital computer 602 may also include one or more input/output devices(s) 614 such as a keyboard, a pointing device, a touchscreen, a microphone, a camera, a display, a speaker, a printer, and the like.

A homology directed repair (HDR) template designer 616 may be included as part of the digital computer 602, for example, as instructions stored in the memory 612. The HDR template designer 616 may design homologous repair templates based on sequences of target sites, sequences of dsDNA molecules, encoding schemes, enzyme recognition sites, etc. In one implementation, the HDR template designer 616 may design homologous repair templates to avoid cross talk between different encoding schemes. The HDR template designer 616 may also compare percent similarity and hybridization conditions for potential homologous repair templates as well as portions of the homologous repair templates. For example, the HDR template designer 616 may design homologous repair templates to avoid the formation of hairpins as well as to prevent or minimize annealing between homologous repair templates. The HDR template designer 616 may also design homologous repair templates to maximize a difference between the 3'-end sequence, 5'-end sequence, and/or middle sequence. For example, the difference may be G:C content and the HDR template designer 616 may design sequences with a preference for increasing the G:C content difference between the end sequences and the middle sequence.

The digital computer 602 may also include an encoding database 618. However, the encoding database 618 may be part of a hardware device that is physically separate from the digital computer 602. The encoding database 618 includes the correspondence between a DNA sequence and a binary value. For example, the information included in Table 1 is one example of an encoding that may be stored in the encoding database 618. The encoding database 618 may store any number of different encodings. The encoding database 618 may be referenced by the HDR template designer 616 to determine which HDR template is to be used next in order to encode a given bit. Similarly, a decoder 620 may also reference the encoding database 618 to determine what bit value to assign to a given sequence. The decoder 620 may be implemented as instructions stored in the memory 612. Thus, sequence data 622 may be provided to the decoder 620 which converts the sequence data 622 into binary data 624.

The decoder 620 may also provide error correction. In implementations in which binary data 624 is redundantly encoded either by writing with a same encoding scheme in multiple target sites or by writing the same binary data 624 in multiple encoding schemes, the decoder 620 may identify the most probable sequence out of multiple different sequences all representing the same binary data 624. Therefore, areas which may be present in some of the sequences will be corrected if a majority of the sequences include the correct value for a given bit.

The decoder 620 may provide error correction through other techniques such as the use of parity bits and block codes. A parity bit is bit added to a string of binary code that indicates whether the number of 1-bits in the string is even or odd. Parity bits are simple forms of error detecting code. In the case of even parity, for a given set of bits, the occurrences of bits whose value is 1 is counted. If that count is odd, the parity bit value is set to 1, making the total count of occurrences of 1's in the whole set (including the parity bit) an even number. If the count of 1's in a given set of bits is already even, the parity bit's value is 0. In the case of odd parity, the coding is reversed. For a given set of bits, if the count of bits with a value of 1 is even, the parity bit value is set to 1 making the total count of 1's in the whole set (including the parity bit) an odd number. If the count of bits with a value of 1 is odd, the count is already odd so the parity bit's value is 0. Thus, by using homologous repair templates to add parity bits based on the binary sequence that is intended to be encoded, reading of the binary data 624 from a DNA sequence will reproduce those parity bits and this may be used by the decoder 620 as one way of identifying an error.

There are many types of block codes such as Reed-Solomon codes, Hamming codes, Hadamard codes, Expander codes, Golay codes, and Reed-Muller codes. The term block code may also refer to any error-correcting code that acts on a block of k bits of input data to produce n bits of output data (n, k). Block codes may be applied in the conventional manner with the message being the intended string of binary data 624 and the noise from the communication channel being introduced either in the incorporation of homologous repair templates into dsDNA or in sequencing of the DNA.

Errors may be introduced in multiple ways including errors from DNA polymerases, nonspecific and unintended annealing, errors in the synthesis of homologous repair templates, and errors in reads generated by DNA sequencing. These types of errors are known to those of skill in the art and may be mitigated by conventional techniques.

Some errors specific to the techniques of this disclosure include insertion of an incorrect homologous repair template and failure to insert the correct homologous repair template. For example, if a DSB is created at a target site $X_1X_2$ then any homologous repair template of the format $X_1\_\_X_2$ may hybridize with the dsDNA on either side of the DSB. If, in order to encode the next bit, the homologous repair template $X_1Y_1Y_2X_2$ should be incorporated into the dsDNA through HDR but instead the homologous repair template $X_1Z_1Z_2X_2$ is incorporated, this will lead to the dsDNA encoding an incorrect bit. The wrong homologous repair template may be available for incorporation because it remains from a previous iteration. Therefore, error rates can be reduced by removing unincorporated homologous repair templates between each iteration. Another type of error may occur when a homologous repair template should be incorporated but it is not. For example, after creation of a DSB in dsDNA at the two ends of the cuts DNA may rejoin each other. This results in the target site that was recently cut reforming. The next iteration may use an enzyme that does not recognize this target site. Therefore, several iterations may pass before an enzyme that recognizes the target site is next brought into contact with the dsDNA. At that point, the dsDNA will be cut and the process of incorporating homologous repair templates will continue. But a number of homologous repair templates will have been missed and the final binary data 624 will omit a number of bits.

In order to manipulate the DNA and potentially RNA that makes up the homologous repair templates and dsDNA, the digital computer 602 may communicate with other devices through one or more I/O data interfaces 626. The I/O Data interface(s) 626 can exchange instructions and data with other devices such as the oligonucleotide synthesizer 604, the automated system 606, the polynucleotide sequencer 608.

The oligonucleotide synthesizer 604 chemically synthesizes oligonucleotides based on instructions received as electronic data. The synthesized oligonucleotides may be used as homologous repair templates. Thus, in some implementations, the sequence of nucleotides which is provided to the oligonucleotide synthesizer 604 may come from the HDR template designer 616.

A number of methods for DNA synthesis and commercial oligonucleotide synthesizers are available. Methods for DNA synthesis include solid-phase phosphoramidite synthesis, microchip-based oligonucleotide synthesis, ligation-mediated assembly, polymerases chain reaction PCR-mediated assembly, and the like. For example, such synthesis can be performed using an ABI 394 DNA Synthesizer (Applied Biosystems, Foster City, Calif.) in 0.2 µmol scale followed by standard cleavage and deprotection protocol, e.g., using 28% aqueous ammonia or a 3:1 solution of ammonia in methanol. One having ordinary skill in the art can select other cleaving agents, such as methylamine, to be used instead of, or in addition to, ammonia, if desired.

The term "oligonucleotide" as used herein is defined as a molecule including two or more nucleotides. Oligonucleotides include probes and primers. Oligonucleotides used as probes or primers may also include nucleotide analogues such as phosphorothioates, alkylphosphorothioates, peptide nucleic acids, or intercalating agents. The introduction of these modifications may be advantageous in order to positively influence characteristics such as hybridization kinetics, reversibility of the hybrid-formation, stability of the oligonucleotide molecules, and the like.

The automated system 606 may include any type of robotics, automation, or other system for automating one or more manipulations that may be performed on the dsDNA with the enzymes and/or the homologous repair templates. The automated system 606 may be used in conjunction with manual operations such that the totality of operations needed to be performed to practice the techniques of this disclosure are done so in a hybrid manner in which some are performed by the automated technique and others manually.

In one implementation, the automated system 606 may include a microfluidics system. Microfluidics is a multidisciplinary field intersecting engineering, physics, chemistry, biochemistry, nanotechnology, and biotechnology, with practical applications to the design of systems in which small volumes of fluids will be handled. Typically, fluids are moved, mixed, separated, or otherwise processed. Numerous applications employ passive fluid control techniques like capillary forces. In some applications, external actuation is additionally used for a directed transport of the media. Examples of external actuation include rotary drives applying centrifugal forces for the fluid transport on the passive chips. Active microfluidics refers to the defined manipulation of the working fluid by active (micro) components such as micropumps or micro valves. Micro pumps supply fluids in a continuous manner or are used for dosing. Micro valves determine the flow direction or the mode of movement of pumped liquids. Often processes which are normally carried out in a lab are miniaturized on a single chip in order to enhance efficiency and mobility as well as reducing sample and reagent volumes. As used herein, the automated system 606 may include other equipment for manipulating DNA.

The automated system 606 may include a cell-free system that can be implemented in part by microfluidics. The cell-free system may also be implemented as an artificial cell or a minimal cell. An artificial cell or minimal cell is an engineered particle that mimics one or many functions of a biological cell. Artificial cells are biological or polymeric membranes which enclose biologically active materials. As such, nanoparticles, liposomes, polymersomes, microcapsules, detergent micelles, and a number of other particles may be considered artificial cells. Micro-encapsulation allows for metabolism within the membrane, exchange of small molecules and prevention of passage of large substances across it. Membranes for artificial cells can be made of simple polymers, crosslinked proteins, lipid membranes or polymer-lipid complexes. Further, membranes can be engineered to present surface proteins such as albumin, antigens, Na/K-ATPase carriers, or pores such as ion channels. Commonly used materials for the production of membranes include hydrogel polymers such as alginate, cellulose and thermoplastic polymers such as hydroxyethyl methacrylate-methyl methacrylate (HEMA-MMA), polyacrylonitrile-polyvinyl chloride (PAN-PVC), as well as variations of the above-mentioned materials.

Minimal cells, also known as proto-cells, are cells that help all the minimum requirements for life. Minimal cells may be created by a top-down approach that knocks out genes in a single-celled organism until a minimal set of genes necessary for life are identified. *Mycoplasma mycoides*, *E. coli*, and *Saccharomyces cerevisiae*, are examples of organisms that may be modified to create minimal cells.

The cell-free system includes components for DNA replication and repair such as nucleotides, DNA polymerase, and DNA ligase. The cell free system will also include dsDNA that includes at least one initial target site for creating a DSB. The dsDNA may be present in the vector that includes one or more operons. The cell free system will also include buffers to maintain pH and ion availability. Furthermore, the cell-free system may also include the enzymes used for creating DSBs in dsDNA and the homologous repair templates used for repairing dsDNA. Some cell free systems may include genes encoding the enzymes and homologous repair templates. To prevent enzymes from remaining when their respective cutting functions are no longer desired, the cell free system may include proteolytic enzymes that specifically break down the DNA cutting enzymes.

In a cell free system, particular components may be added when needed either by moving volumes of liquid together with microfluidics or by increasing the expression of gene products that leads to synthesis of enzymes, homologous repair templates, etc.

The automated system 606 may include a structure, such at least one chamber which holds one or more DNA molecules. The chamber may be implemented as any type of mechanical, biological, or chemical arrangement which holds a volume of liquid including DNA to a physical location. For example, a single flat surface having a droplet present thereon, with the droplet held in part by surface tension of the liquid, even though not fully enclosed within a container, is one implementation of a chamber.

The automated system 606 may perform many types of manipulations on DNA molecules. For example, the automated system 606 may be configured to move a volume of liquid from the chamber to another chamber in response to a series of instructions from the I/O data interface 626.

Microfluidics systems and methods to divide a bulk volume into partitions include emulsification, generation of "water-in-oil" droplets, and generation of monodispersed droplets as well as using channels, valves, and pumps. Partitioning methods can be augmented with droplet manipulation techniques, including electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). In some embodiments, a droplet microactuator is supplemented with a microfluidics platform (e.g. continuous flow components). Some implementations of microfluidics systems use a droplet microactuator. A droplet microactuator can be capable of effecting droplet manipulation and/or operations, such as dispensing, splitting, transporting, merging, mixing, agitating, and the like.

The polynucleotide sequencer 608 may sequence DNA molecules using any technique for sequencing nucleic acids known to those skilled in the art. The polynucleotide sequencer 608 may be configured to sequence all or part of a dsDNA molecule modified according to any of the techniques described above and provide the sequence data 622 to the digital computer 602.

DNA sequencing techniques include classic dideoxy sequencing reactions (Sanger method) using labeled terminators or primers and gel separation in slab or capillary electrophoresis. In one implementation, next generation (NextGen) sequencing platforms are advantageously used in the practice of the invention. NextGen sequencing refers to any of a number of post-classic Sanger type sequencing methods which are capable of high throughput, multiplex sequencing of large numbers of samples simultaneously. Current NextGen sequencing platforms are capable of generating reads from multiple distinct nucleic acids in the same sequencing run. Throughput is varied, with 100 million bases to 600 giga bases per run, and throughput is rapidly increasing due to improvements in technology. The principle of operation of different NextGen sequencing platforms is also varied and can include: sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real-time monitoring of the incorporation of labeled nucleotides during a polymerization step, polony sequencing, single molecule real-time sequencing, nanopore sequencing, and SOLiD sequencing.

454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains a 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

A sequencing technique that can be used is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm'. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step.

Another example of a DNA sequencing technique that can be used is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

Another example of a sequencing technology that can be used is SOLEXA sequencing (Illumina). SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technology that can be used includes the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing. A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

The sequence data 622 generated by sequencing can be sent from the polynucleotide sequencer 608 to the digital computer 602 for decoding by the decoder 620 and also for presentation on an output device 614.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document, "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method for encoding binary data in a double stranded deoxyribose nucleic acid (dsDNA), the method comprising:
creating a first double strand break (DSB) at a first target site in the dsDNA with a first enzyme;
selecting a first homologous repair template according to a first binary digit, the first target site, and an encoding scheme; and
contacting the dsDNA with the first homologous repair template,
wherein the first homologous repair template contains a region complementary to a second target site for a second enzyme to create a second DSB in the dsDNA and the first binary digit is encoded by an order of a partial sequence of the first target site being adjacent to a partial sequence of the second target site.

Clause 2. The method of clause 1, wherein the first target site is unique in the dsDNA prior to the first DSB.

Clause 3. The method of any of clauses 1 or 2, wherein the first enzyme comprises a restriction enzyme, a CRISPR/Cas system, a TALEN, a zinc finger, or any other protein-protein complex, protein-RNA complex, or protein-protein-RNA complex capable of cutting dsDNA at a specific DNA sequence.

Clause 4. The method of any clauses 1-3, wherein:
a DNA sequence of the first target site comprises a first subsequence that is repeated once; and
the first homologous repair template comprises:
a 3'-end sequence and a 5'-end sequence each encoding a second subsequence that is complementary to the first subsequence; and
two adjacent instances of a third subsequence in the middle of the first homologous repair template.

Clause 5. The method of any of clauses 1-4, wherein the first homologous repair template is selected from two potential homologous repair templates, wherein, according to the encoding scheme, DNA complementary to a first portion of the two potential homologous repair templates represents the binary digit 0 when adjacent to the partial sequence of the first target site and DNA complementary to a second portion of the two potential homologous repair templates represents the binary digit 1 when adjacent to the partial sequence of the first target site.

Clause 6. The method of any of clauses 1-5, further comprising generating the first homologous repair template by oligonucleotide synthesis.

Clause 7. The method of any of clauses 1-6, further comprising generating the first homologous repair template from a ribonucleic acid (RNA) sequence using reverse transcriptase.

Clause 8. The method of clause 7, wherein contacting the dsDNA with the first homologous repair template comprises upregulating expression of a gene coding for the RNA sequence.

Clause 9. The method of any of clauses 1-8, further comprising:
generating a sequence file by sequencing the dsDNA after homologous repair of the first DSB with the homologous repair template; and
interpreting the sequence file to identify the first binary digit based on the encoding scheme.

Clause 10. The method of any of clauses 1-9, further comprising:
creating the second DSB at the second target site in the dsDNA with the second enzyme;
selecting a second homologous repair template according to a second binary digit, the second target site, and the encoding scheme; and
contacting the dsDNA with the second homologous repair template,
wherein the second homologous repair template contains a third target site for a third enzyme to create a third DSB in the dsDNA and the second binary digit is encoded by an order of the partial sequence of the second target site followed by a partial sequence of the third target site.

Clause 11. The method of clause 10, further comprising, after the contacting the dsDNA with the first homologous repair template and before the contacting the dsDNA with the second homologous repair template, at least one of:
washing the dsDNA to remove the first homologous repair template; or waiting a length of time sufficient for a concentration of the first homologous repair template to decrease below a threshold level.

Clause 12. The method of any of clauses 1-11, wherein contacting the dsDNA with the first homologous repair template comprises transforming a cell containing the dsDNA with the first homologous repair template thereby introducing the dsDNA into the cell, wherein the first homologous repair template is exogenous to the cell.

Clause 13. A cell capable of heritably storing binary data, the cell comprising:
- a dsDNA molecule comprising a first target site;
- a first enzyme configured to create a DSB within the first target site;
- a gene under the control of a promoter and operator that encodes a RNA sequence comprising a 3'-end sequence and a 5'-end sequence;
- a homologous repair template generated from the gene, the homologous repair template being either:
  (i) the RNA sequence, wherein the 3'-end sequence and 5'-end sequence are complementary to one strand of the dsDNA molecule over at least a part of the first target site, or
  (ii) a ssDNA sequence complementary to the RNA sequence, wherein the 3'-end sequence and the 5'-end sequence are complementary to one strand of the dsDNA molecule over at least a part of the first target site; and
- an engineered signaling pathway that changes a rate of transcription of the RNA sequence in response to an intracellular or extracellular signal.

Clause 14. The cell of clause 13, wherein the first enzyme is a CRISPR/Cas system comprising a guide RNA (gRNA) that includes a spacer region complementary to one strand of the dsDNA at the first target site.

Clause 15. The cell of any of clauses 13 or 14, wherein the homologous repair template comprises a region that is complementary to a second target site such that repair of the DSB within the first target site by the homologous repair template introduces the second target site into the dsDNA molecule, the second target site used by a second enzyme to create a DSB within the second target site.

Clause 16. The cell of any of clauses 13-15, wherein the engineered signaling pathway comprises at least one of a G protein-coupled receptor, a photoreceptor, a thermosensor, or a membrane-bound immunoglobulin (mIg).

Clause 17. The cell of any of clauses 13-16, further comprising an additional dsDNA molecule that comprises an additional instance of the target site, wherein the dsDNA molecule contains only a single instance of the target site and the additional dsDNA molecule contains only a single instance of the target site.

Clause 18. A method comprising:
- creating a first DSB in a first target site in a dsDNA with a first enzyme;
- contacting the dsDNA with a first homologous repair template comprising a 3'-end sequence complementary to a first portion of the first target site and a 5'-end sequence complementary to a second portion of the first target site, wherein a portion of the first target site adjacent to a portion of dsDNA generated by repair of the first DSB encodes a first binary digit according to a first encoding scheme and a DNA sequence complementary to a middle portion of the first homologous repair template comprises a second target site according to the first encoding scheme;
- creating a second DSB in a third target site in the dsDNA with a second enzyme, the third target site having a different sequence than the first target site and being at least one base pair (bp) removed from the first target site; and
- contacting the dsDNA with a second homologous repair template comprising a 3'-end sequence complementary to a first portion of the third target site and a 5'-end sequence complementary to a second portion of the third target site, wherein a sequence of a portion of the third target site adjacent to a portion of the dsDNA generated by repairing the second DSB encodes a second binary digit according to a second encoding scheme and a DNA sequence complementary to a middle portion of the second homologous repair template comprises a fourth target site according to the second encoding scheme.

Clause 19. The method of clause 18, wherein the first encoding scheme is orthogonal to the second encoding scheme such that target sites belonging to the first target site and second target site are both different than either the third target site or the fourth target site.

Clause 20. The method of any of clauses 18 or 19, wherein the method is implemented at least in part in a cell-free system, the dsDNA is a circular dsDNA molecule, and the contacting the dsDNA with the first homologous repair template comprises activating a microfluidic mechanism to move the first homologous repair template into a same chamber as the dsDNA.

CONCLUSION

The terms "a," "an," "the" and similar referents used in the context of describing the invention (especially in the context of the following claims) are to be construed to cover both the singular and the plural, unless otherwise indicated herein or clearly contradicted by context.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for their particular cited teachings as well as for all that they disclose.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The invention claimed is:

1. A method for encoding a binary digit in a double stranded deoxyribose nucleic acid (dsDNA), the method comprising:
    creating a first double strand break (DSB) at a first target site in the dsDNA with a first enzyme;
    selecting a first homologous repair template according to a first binary digit, the first target site, and an encoding scheme; and
    contacting the dsDNA with the first homologous repair template,
    wherein the first homologous repair template contains a region complementary to a second target site for a second enzyme to create a second DSB in the dsDNA and the first binary digit is encoded by an order of a partial sequence of the first target site being contiguous to a partial sequence of the second target site, wherein the partial sequence of the first target site and the partial sequence of the second target site are both independently between 5 and 20 nucleotides.

2. The method of claim 1, wherein the first target site is unique in the dsDNA at the time of making the first DSB.

3. The method of claim 1, wherein the first enzyme comprises a restriction enzyme, a clustered regularly interspaced short palindromic repeats/CRISPR associated protein (CRISPR/Cas) nuclease, a transcription activator-like effector nuclease (TALEN), homing endonuclease (HE), or a zinc finger nuclease (ZFN).

4. The method of claim 1, wherein:
    a DNA sequence of the first target site comprises a first subsequence that is repeated once; and
    the first homologous repair template comprises:
    a 3'-end sequence and a 5'-end sequence each encoding a second subsequence that is complementary to the first subsequence; and
    two adjacent instances of a third subsequence in the first homologous repair template between the 3'-end sequence and the 5'-end sequence.

5. The method of claim 1, wherein the first homologous repair template is selected from two potential homologous repair templates, wherein, according to the encoding scheme, DNA complementary to a first portion of the two potential homologous repair templates represents the binary digit 0 when adjacent to the partial sequence of the first target site and DNA complementary to a second portion of the two potential homologous repair templates represents the binary digit 1 when adjacent to the partial sequence of the first target site.

6. The method of claim 1, further comprising generating the first homologous repair template by oligonucleotide synthesis.

7. The method of claim 1, further comprising generating the first homologous repair template from a ribonucleic acid (RNA) sequence using reverse transcriptase.

8. The method of claim 7, wherein contacting the dsDNA with the first homologous repair template comprises upregulating expression of a gene coding for the RNA sequence.

9. The method of claim 1, further comprising:
    generating a sequence file by sequencing the dsDNA after homologous repair of the first DSB with the first homologous repair template; and
    interpreting the sequence file to identify the first binary digit based on the encoding scheme.

10. The method of claim 1, further comprising:
    creating the second DSB at the second target site in the dsDNA with the second enzyme;
    selecting a second homologous repair template according to a second binary digit, the second target site, and the encoding scheme; and
    contacting the dsDNA with the second homologous repair template,
    wherein the second homologous repair template contains a third target site for a third enzyme to create a third DSB in the dsDNA and the second binary digit is encoded by an order of the partial sequence of the second target site followed by a partial sequence of the third target site.

11. The method of claim 10, further comprising, after the contacting the dsDNA with the first homologous repair template and before the contacting the dsDNA with the second homologous repair template, at least one of:
    washing the dsDNA to remove the first homologous repair template; or
    waiting a length of time sufficient for a concentration of the first homologous repair template to decrease below a threshold level.

12. The method of claim 1, wherein contacting the dsDNA with the first homologous repair template comprises transforming a cell containing the dsDNA with the first homologous repair template thereby introducing the dsDNA into the cell, wherein the first homologous repair template is exogenous to the cell.

13. A method comprising:
    creating a first DSB in a first target site in a dsDNA with a first enzyme;
    contacting the dsDNA comprising the first DSB with a first homologous repair template comprising a 3'-end sequence complementary to a first portion of the first target site and a 5'-end sequence complementary to a second portion of the first target site,
    wherein the first portion of the first target site and the second portion of the first target site are both independently between 5 and 20 nucleotides,
    wherein a portion of the first target site contiguous to dsDNA generated by repair of the first DSB encodes a first binary digit according to a first encoding scheme and a DNA sequence complementary to a sequence between the 3'-end sequence and the 5'-end sequence of the first homologous repair template comprises a second target site according to the first encoding scheme;
    creating a second DSB in a third target site in the dsDNA with a second enzyme, the third target site having a different sequence than the first target site and being at least one base pair (bp) removed from the first target site; and
    contacting the dsDNA with a second homologous repair template comprising a 3'-end sequence complementary to a first portion of the third target site and a 5'-end sequence complementary to a second portion of the third target site,
    wherein the first portion of the third target site and the second portion of the third target site are both independently between 5 and 20 nucleotides,
    wherein a sequence of between 5 and 20 nucleotides of the third target site adjacent to the dsDNA generated by repairing the second DSB encodes a second binary digit according to a second encoding scheme and a DNA sequence complementary to a sequence between the 3'-end sequence and the 5'-end sequence of the second homologous repair template comprises a fourth target site according to the second encoding scheme.

14. The method of claim 13, wherein the first encoding scheme is orthogonal to the second encoding scheme such that target sites belonging to the first target site and the second target site are both different than either the third target site or the fourth target site.

15. The method of claim 13, wherein the method is implemented at least in part in a cell-free system, the dsDNA is a circular dsDNA molecule, and the contacting the dsDNA with the first homologous repair template comprises activating a microfluidic mechanism to move the first homologous repair template into a same chamber as the dsDNA.

16. A method of encoding binary data in a polynucleotide within a cell, the method comprising:
receiving a first external signal that represents a first binary digit;
inserting a first homology directed repair (HDR) template into a double-stranded polynucleotide by HDR, the first HDR template having a first sequence that is assigned a first value of the first binary digit according to a context-dependent code in which a value of a binary digit is represented by both a sequence inserted by an HDR template using HDR and a target sequence into which the HDR template is inserted;
generating a first molecular signal based on the first binary digit, wherein presence of the first molecular signal places the cell into a first state;
receiving a second external signal that represents a second binary digit; and
inserting a second HDR template, by HDR, into a cut site created by insertion of the first HDR template, the second HDR template having a second sequence that is assigned a second value of the second binary digit according to the context-dependent code and based on the cell being in the first state.

17. The method of claim 16, wherein the first molecular signal comprises a transcription factor that activates a promoter associated with the first state of the cell.

18. The method of claim 16, wherein the second HDR template comprises a 3'-end sequence and a 5'-end sequence that are homologous to portions of a target site on the double-stranded polynucleotide, and a middle region that comprises an identifier region that represents the second binary digit and an additional target site having a sequence based on the first state.

19. The method of claim 16, wherein the context-dependent code prevents adjacent insertions of a same polynucleotide sequence into the double-stranded polynucleotide.

20. The method of claim 16, further comprising:
generating a second molecular signal based on the second binary digit, presence of the second molecular signal placing the cell into a second state different than the first state;
receiving a third external signal that represents a third binary digit; and
inserting a third HDR template, by HDR, into a cut site created by insertion of the second HDR template, the third HDR template having a third sequence assigned a third value of the third binary digit according to the context-dependent code and based on the cell being in the second state.

21. The method of claim 20, wherein the first state is a first stable state of a bi-stable molecular switch and the second state is a second stable state of the bi-stable molecular switch.

* * * * *

```
                              SEQUENCE LISTING

<160> NUMBER OF SEQ ID NOS: 9

<210> SEQ ID NO 1
   <211> LENGTH: 21
   <212> TYPE: DNA
   <213> ORGANISM: Artificial Sequence
   <220> FEATURE:
   <223> OTHER INFORMATION: X1 example

<400> SEQUENCE: 1
tagccgtatc gagcatcgat g                                          21

<210> SEQ ID NO 2
   <211> LENGTH: 11
   <212> TYPE: DNA
   <213> ORGANISM: Artificial Sequence
   <220> FEATURE:
   <223> OTHER INFORMATION: X2 example
   <220> FEATURE:
   <221> NAME/KEY: misc_feature
   <222> LOCATION: (4)..(7)
   <223> OTHER INFORMATION: n is a, c, g, or t

<400> SEQUENCE: 2
cgcnnnngat t                                                     11

<210> SEQ ID NO 3
   <211> LENGTH: 21
   <212> TYPE: DNA
   <213> ORGANISM: Artificial Sequence
   <220> FEATURE:
   <223> OTHER INFORMATION: Y1 example

<400> SEQUENCE: 3
gatcgatgga ctctgcatct a                                          21

<210> SEQ ID NO 4
   <211> LENGTH: 11
   <212> TYPE: DNA
   <213> ORGANISM: Artificial Sequence
   <220> FEATURE:
   <223> OTHER INFORMATION: Y2 example
   <220> FEATURE:
   <221> NAME/KEY: misc_feature
   <222> LOCATION: (4)..(7)
   <223> OTHER INFORMATION: n is a, c, g, or t

<400> SEQUENCE: 4
tcgnnnngat t                                                     11

<210> SEQ ID NO 5
   <211> LENGTH: 21
   <212> TYPE: DNA
   <213> ORGANISM: Artificial Sequence
   <220> FEATURE:
   <223> OTHER INFORMATION: Z1 example

<400> SEQUENCE: 5
```

-continued

```
cgggacgatc gatcgggcta g                                              21

<210> SEQ ID NO 6
<211> LENGTH: 11
<212> TYPE: DNA
<213> ORGANISM: Artificial Sequence
<220> FEATURE:
<223> OTHER INFORMATION: Z2 example
<220> FEATURE:
<221> NAME/KEY: misc_feature
<222> LOCATION: (4)..(7)
<223> OTHER INFORMATION: n is a, c, g, or t

<400> SEQUENCE: 6
actnnnngat t                                                         11

<210> SEQ ID NO 7
<211> LENGTH: 64
<212> TYPE: DNA
<213> ORGANISM: Artificial Sequence
<220> FEATURE:
<223> OTHER INFORMATION: Homology directed repair sequences of X1Y1Y2X2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t

<400> SEQUENCE: 7
tagccgtatc gagcatcgat ggatcgatgg actctgcatc tatcgnnnng attcgcnnnn     60
gatt                                                                 64

<210> SEQ ID NO 8
<211> LENGTH: 64
<212> TYPE: DNA
<213> ORGANISM: Artificial Sequence
<220> FEATURE:
<223> OTHER INFORMATION: Homology directed repair sequences Y1X1X2Y2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t

<400> SEQUENCE: 8
gatcgatgga ctctgcatct atagccgtat cgagcatcga tgcgcnnnng atttcgnnnn     60
gatt                                                                 64

<210> SEQ ID NO 9
<211> LENGTH: 12
<212> TYPE: DNA
<213> ORGANISM: Artificial Sequence
<220> FEATURE:
<223> OTHER INFORMATION: Repeated subsequence in target sequence example

<400> SEQUENCE: 9
gtactagtac ta                                                        12
```